(12) United States Patent
Shin

(10) Patent No.: US 10,314,341 B2
(45) Date of Patent: Jun. 11, 2019

(54) ELECTRONIC CIGARETTE HAVING AN ELEVATING PORTION

(71) Applicant: Jong-Soo Shin, Cheongju-si (KR)

(72) Inventor: Jong-Soo Shin, Cheongju-si (KR)

( * ) Notice: Subject to any disclaimer, the term of this patent is extended or adjusted under 35 U.S.C. 154(b) by 40 days.

(21) Appl. No.: 15/535,357

(22) PCT Filed: Nov. 25, 2015

(86) PCT No.: PCT/KR2015/012686
§ 371 (c)(1),
(2) Date: Jun. 12, 2017

(87) PCT Pub. No.: WO2016/099045
PCT Pub. Date: Jun. 23, 2016

(65) Prior Publication Data
US 2017/0347708 A1 Dec. 7, 2017

(30) Foreign Application Priority Data
Dec. 16, 2014 (KR) .................. 10-2014-0181873

(51) Int. Cl.
*A24F 13/00* (2006.01)
*A24F 47/00* (2006.01)
*A61M 15/06* (2006.01)

(52) U.S. Cl.
CPC .......... *A24F 47/008* (2013.01); *A24F 47/002* (2013.01); *A61M 15/06* (2013.01)

(58) Field of Classification Search
CPC ...... A24F 47/008; A24F 47/002; A61M 15/06
USPC ................................. 131/329, 328
See application file for complete search history.

(56) References Cited

U.S. PATENT DOCUMENTS

| 9,295,286 B2* | 3/2016 | Shin ............... A24F 47/008 |
| 2011/0226236 A1* | 9/2011 | Buchberger ......... A61M 11/041 |
| | | 128/200.23 |
| 2013/0167854 A1* | 7/2013 | Shin ............... A24F 47/008 |
| | | 131/329 |
| 2016/0050975 A1* | 2/2016 | Worm .............. A24F 47/008 |
| | | 131/328 |
| 2016/0160967 A1* | 6/2016 | Shin ............... F16H 21/44 |
| | | 74/103 |
| 2017/0099877 A1* | 4/2017 | Worm .............. A61M 11/042 |
| 2017/0119053 A1* | 5/2017 | Henry, Jr. ........... A24F 47/008 |

(Continued)

FOREIGN PATENT DOCUMENTS

| KR | 10-1057774 B1 | 8/2011 |
| KR | 10-1084048 B2 | 11/2011 |

(Continued)

OTHER PUBLICATIONS

International Search Report dated Mar. 31, 2016, issued in PCT Application No. PCT/KR2015/012686, filed Nov. 25, 2015.

(Continued)

*Primary Examiner* — Hae Moon Hyeon
(74) *Attorney, Agent, or Firm* — Workman Nydegger

(57) ABSTRACT

An electronic cigarette includes: a power supply portion which supplies power to the electronic cigarette; an elevating portion being controllable up and down by the supplied power; a smoke generating portion coupled to the elevating portion to be movable up and down; and a connector portion which connects between the smoke generating portion and the elevating portion.

13 Claims, 36 Drawing Sheets

(56) References Cited

U.S. PATENT DOCUMENTS

2017/0150757 A1\* 6/2017 Worm .................... A24F 47/008
2018/0132526 A1\* 5/2018 Davis .................... A24F 47/008

FOREIGN PATENT DOCUMENTS

| KR | 10-2013-0031025 A | 3/2013 |
| KR | 10-1285225 B1 | 7/2013 |
| KR | 20-2014-0002774 U | 5/2014 |

OTHER PUBLICATIONS

Written Opinion dated Mar. 31, 2016, issued in PCT Application No. PCT/KR2015/012686, filed Nov. 25, 2015.

\* cited by examiner

ELECTRONIC CIGARETTE HAVING AN ELEVATING PORTION

CROSS-REFERENCE TO RELATED APPLICATION

This application is a 371 National Stage of PCT Application No. PCT/KR2015/012686, filed Nov. 25, 2015, which claims priority to Korean Application No. 10-2014-0181873, filed Dec. 16, 2014, the entirety of each of the foregoing applications being incorporated hereby by specific reference.

BACKGROUND

Technical Field

The present invention relates to an electronic cigarette and, more specifically, to an electronic cigarette comprising: a power supply portion which supplies power to the electronic cigarette; an elevating portion being controllable up and down by the supplied power; a smoke generating portion being movable up and down by being coupled to the elevating portion; and a connector portion which connects the smoke generating portion to the elevating portion. According to the present invention, the power supply portion simplifies the structure of a product and improves utilization efficiency of a battery by using a contact pin and a center pin in connecting power between the power supply portion and the smoke generating portion. Also, according to the present invention, the contact pin and the center pin having a pop-up pin structure including an elastic body inside enable a connection state of power connecting portions to be stably maintained. Moreover, according to the present invention, when a user holds and turns an upper region of the smoke generating portion to separate the smoke generating portion, the connection between the connector portion and the elevating portion is released before the connection between the smoke generating portion and the connector portion is disengaged, thereby preventing a solution inside the smoke generating portion from being spilled.

The Relevant Technology

Smoke of typical cigarettes, such as a cigarette, a cigar, and pipe tobacco, contain a number of toxic chemicals to a human body, such as tar, hydrocarbon, and carbon monoxide. For this reason, smoke of typical cigarettes causes various diseases, like lung cancer or circulatory system diseases and damages the health of a smoker. Also, secondhand smoking puts non-smokers around at health risk, caused by smoke exhaled by the smoker during smoking and harmful chemicals lingering in places of smoking. Accordingly, policies for lowering smoking rates and encouraging quitting smoking, such as reinforcing regulations on tobacco sales and limiting smoking areas unlike the past, are being enforced all over the world. However, in practice, smokers cannot easily quit smoking because they are addicted to nicotine contained in tobacco.

In this respect, an electronic cigarette was recently developed and has been sold, which generates smoke by vaporizing a solution that contains nicotine and does not contain toxic compounds, like tar, included in the typical cigarettes. The electronic cigarette which discharges less toxic smoke while satisfying a desire to smoke for the smoker can reduce damage in smokers and secondhand smokers and function as a supplementary means for smoking cessation for those who want to quit smoking.

Generally, in the electronic cigarette, internal elements are connected by wires and supplied with power and turning power on and off can be controlled by using a separate switch. In such cases, there is a problem in that the internal structure of the electronic cigarette becomes complicated and utilization efficiency decreases since a battery can be discharged even when the power is off.

In addition, when a user holds and turns an upper end of the electronic cigarette to separate a cartridge of the electronic cigarette for refilling a nicotine solution, the whole cartridge is not fully separated, but an atomizer portion which generates smoke inside the cartridge can be separated. In this case, the nicotine solution stored inside the cartridge can be spilled, which is problematic.

Therefore, it is necessary to develop a structure of an electronic cigarette, capable of preventing the nicotine solution from being spilled which can be caused by the unintentionally separated atomizer, while simplifying the internal structure of the electronic cigarette, preventing discharge of a battery, and increasing utilization efficiency.

BRIEF SUMMARY OF THE INVENTION

Technical Problem

The present invention has been made in an effort to solve the problems.

An object of the present invention is to provide an electronic cigarette comprising a power supply portion having a structure capable of supplying power to the inside by a center pin and a contact pin being a conductor without using wires.

Another object of the present invention is to provide an electronic cigarette capable of connecting/disconnecting power by vertical movement of an elevating portion that can move a smoke generating portion of the electronic cigarette upwardly and downwardly.

Yet another object of the present invention is to provide an electronic cigarette capable of preventing discharge of a battery and improving utilization efficiency by connecting/disconnecting power of the electronic cigarette based on contact or separation between a power supply terminal and a contact pin.

Yet another object of the present invention is to provide an electronic cigarette capable of stably maintaining a connecting state of power connection portions by elongating or shrinking the length of a center pin and a contact pin configured to include an elastic body inside a center pin and a contact pin.

Yet another object of the present invention is to provide an electronic cigarette capable of prevent a solution inside a smoke generating portion from being spilled when a user holds and turns an upper region of a smoke generating portion for separating the smoke generating portion.

Other objects and advantages of the present invention can be understood by the following description, and become apparent with reference to the embodiments of the present invention. Also, the objects and advantages of the present invention can be realized by the means as claimed and combinations thereof.

Technical Solutions

In order to achieve the above object, the present invention is realized by embodiments having the following features.

According to one embodiment of the present invention, the electronic cigarette comprises: a smoke generating portion which generates smoke of the electronic cigarette; an elevating portion coupled to the smoke generating portion to be movable in a vertical direction; and a power supply portion which supplies power to the smoke generating portion through the elevating portion, the power supply portion including a battery which generates electrical energy to supply power, a power supply terminal which supplies power supplied from the battery, a center pin being a conductor and a contact pin being a conductor, wherein the contact pin is provided in the elevating portion to be in vertical motion and capable of connecting or disconnecting power by contacting with or separating from the power supply terminal through the vertical motion.

According to another embodiment of the present invention, in the electronic cigarette, the power supply portion comprises: a connecting terminal which connects the contact pin to the center pin; and a main circuit board which controls operation of the power supply terminal and the electronic cigarette, wherein the connecting terminal is provided in the elevating portion.

According to still another embodiment of the present invention, in the electronic cigarette, the power supply portion comprises: a connecting terminal which connects the contact pin to the center pin; and a main circuit board which controls operation of the power supply terminal and the electronic cigarette, wherein the connecting terminal is provided in the elevating portion.

According to still another embodiment of the present invention, in the electronic cigarette, the first connecting terminal includes a first contact pin receiving hole and is coupled to the contact pin, and the second connecting terminal includes a center pin receiving hole and a second contact pin receiving hole, wherein the center pin receiving hole is coupled to the center pin and the second contact pin receiving hole is coupled to the contact pin such that the center pin and the contact pin are in electrical communication.

According to still another embodiment of the present invention, in the electronic cigarette, the contact pin comprises: a first contact pin and a second contact pin, wherein one end of the first contact pin is electrically connected to the first contact pin receiving hole of the first connecting terminal and an end of the second contact pin is electrically connected to the second contact pin receiving hole such that the contact pin electrically contacts with the power supply terminal when the elevating portion ascends and electrical contact is released when the elevating portion descends.

According to still another embodiment of the present invention, in the electronic cigarette, the contact pin and the center pin includes an elastic body inside such that: the contact pin and the center pin are capable of being elastically compressed or elastically restored in a vertical direction; electrical communication is well maintained by pressurizing the power supply terminal by the elastic body when the contact pin contacts with the power supply terminal as the elevating portion ascends; and electrical communication is well maintained by pressurizing the smoke generating portion by the elastic body when the center pin contacts with the smoke generating portion, thereby enabling stable power connection state of the electronic cigarette.

According to still another embodiment of the present invention, in the electronic cigarette, the elevating portion comprises: a support which supports a lower portion of the smoke generating portion; and an elevating body portion formed at one side of the support to control vertical motion of the elevating portion, wherein the elevating body portion includes a contact pin coupling portion capable of receiving the contact pin inside for coupling, and the contact pin is inserted in the contact pin coupling portion and coupled to the elevating portion to be in vertical motion integrally with the elevating portion.

According to still another embodiment of the present invention, in the electronic cigarette, the support includes a center pin coupling portion capable of receiving the center pin for coupling and formed at an upper end, wherein the center pin is inserted in the center pin coupling portion to be coupled to the support and is capable of moving integrally with the support in the coupling state.

According to still another embodiment of the present invention, the electronic cigarette further comprises a connector portion which connects between the smoke generating portion and the elevating portion, wherein an upper end of the connector portion is connectable to the smoke generating portion and a lower end of the connector portion is connectable to the support.

According to still another embodiment of the present invention, in the electronic cigarette, the connector portion comprises a support coupling portion which has a protrusion protruding downward at the lower end, and the support comprises a connector coupling portion protruding upward from a center part of an upper end; and a connector insertion groove by which the support coupling portion is inserted in an outer side of the connector coupling portion, thereby coupling the connector portion with the support as the support coupling portion is inserted in the connector insertion groove while the connector coupling portion is received for coupling in an inner space that the support coupling portion forms.

According to still another embodiment of the present invention, in the electronic cigarette, the connector portion comprises: a support insertion portion protruded in a horizontal direction in an upper side of the support coupling portion; and a support insertion groove, a part of which is depressed inward by a certain depth inside the support insertion portion, wherein the support includes a connector fixing portion protruded upward along the periphery of the upper part of the support, the connector fixing portion including a protrusion, a part of which is protruded toward the center part of the support on a plane, wherein the connector fixing portion is received for coupling in a horizontal direction into the support insertion groove in coupling the connector portion to the support, and after coupling the connector portion is rotated such that the connector fixing portion presses and fixes the support insertion portion, thereby fixing the coupling of the connector portion and the support.

According to still another embodiment of the present invention, in the electronic cigarette, the protrusion of the connector fixing portion includes an inclined surface inclined along a circumferential direction at the lower end, one end of the inclined surface having height lower than the other end, wherein when the connector is inserted in the support and rotated, the support insertion portion proceeds to the other end through the one end of the inclined surface and is pressed by the other end of the inclined surface, whereby the connector is firmly fixed to the support.

Advantageous Effects

According to the above-described embodiments and the following features, combinations, and relations of use that will be described later, the present invention can obtain the following effects.

The electronic cigarette according to the present invention can supply power to the inside by a center pin and a contact pin being a conductor without using wires.

The electronic cigarette according to the present invention can connect/disconnect power by vertical movement of an elevating portion that can move a smoke generating portion of the electronic cigarette.

The electronic cigarette according to the present invention can prevent discharge of a battery and improve utilization efficiency by connecting/disconnecting power of the electronic cigarette based on contact or separation between a power supply terminal and a contact pin.

The electronic cigarette according to the present invention can stably maintain a connecting state of power connection portions by elongating or shrinking the length of a center pin and a contact pin configured to include an elastic body inside a center pin and a contact pin.

The electronic cigarette according to the present invention can prevent a solution inside a smoke generating portion from being spilled when a user holds and turns an upper region of a smoke generating portion for separating the smoke generating portion.

DETAILED DESCRIPTION OF THE INVENTION

Figure 1A:
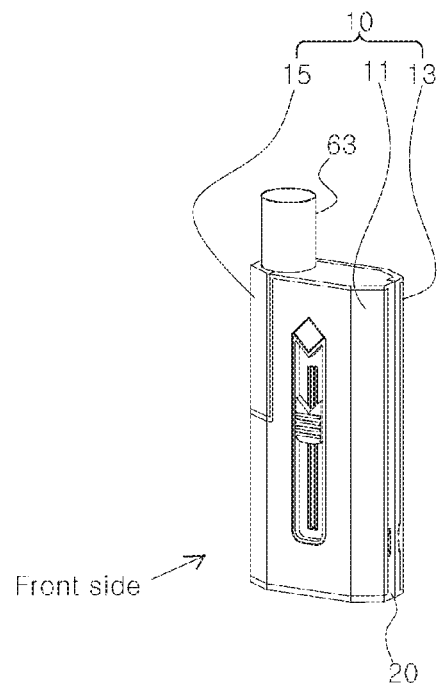
FIG. 1 is a perspective view of an electronic cigarette according to one embodiment of the present invention, shown from a front side.

Hereinafter, an electronic cigarette according to the present invention will be described with reference to accompanying drawings. Unless not specifically defined, all terminologies in the specification should be interpreted based on the general meanings thereof that a person skilled in the art understands. When the general meanings of the terminologies are incompliant with those used in the specification, the terminologies should be interpreted as being defined herein. In describing the present invention, well-known functions or constructions will not be described in detail in case they may unnecessarily obscure the understanding of the present invention.

Also, when a part "includes" or "comprises" an element in the description, unless there is a particular description contrary thereto, the part can further include other elements, not excluding the other elements. In the following description, terms, such as "unit" and "part," indicate a unit or a part for processing at least one function or operation.

Moreover, in describing embodiments of the present invention, a location and movement of each element are defined by a direction expressed by an arrow in the drawings and separately defined in the description if necessary.

Figure 1B:
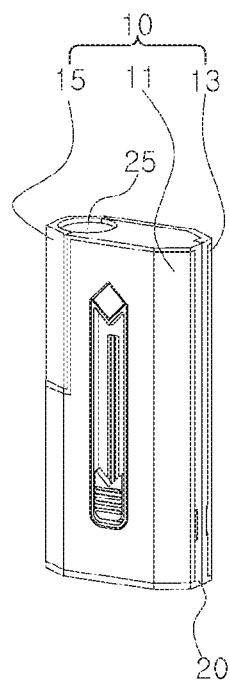
Figure 2:
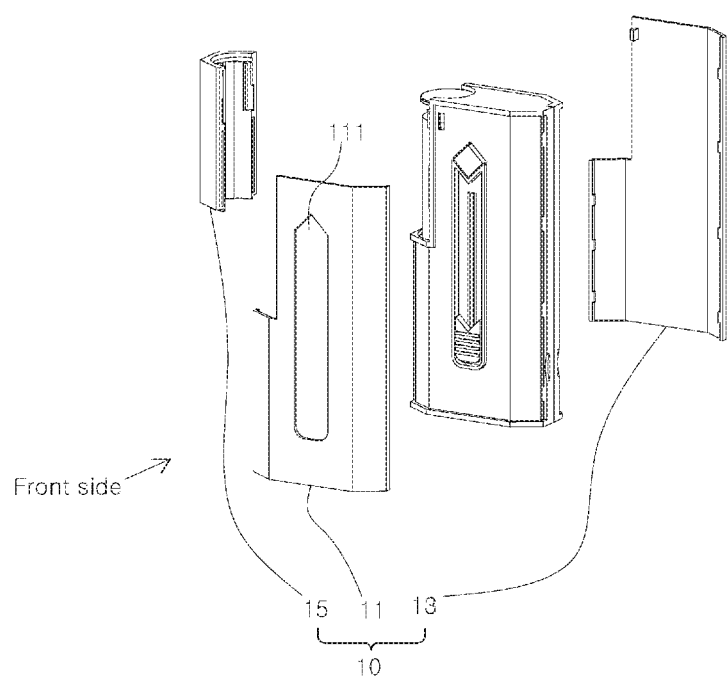
FIGS. 2 to 4 are exploded perspective views of each element of the electronic cigarette according to one embodiment of the present invention.
Figure 3:
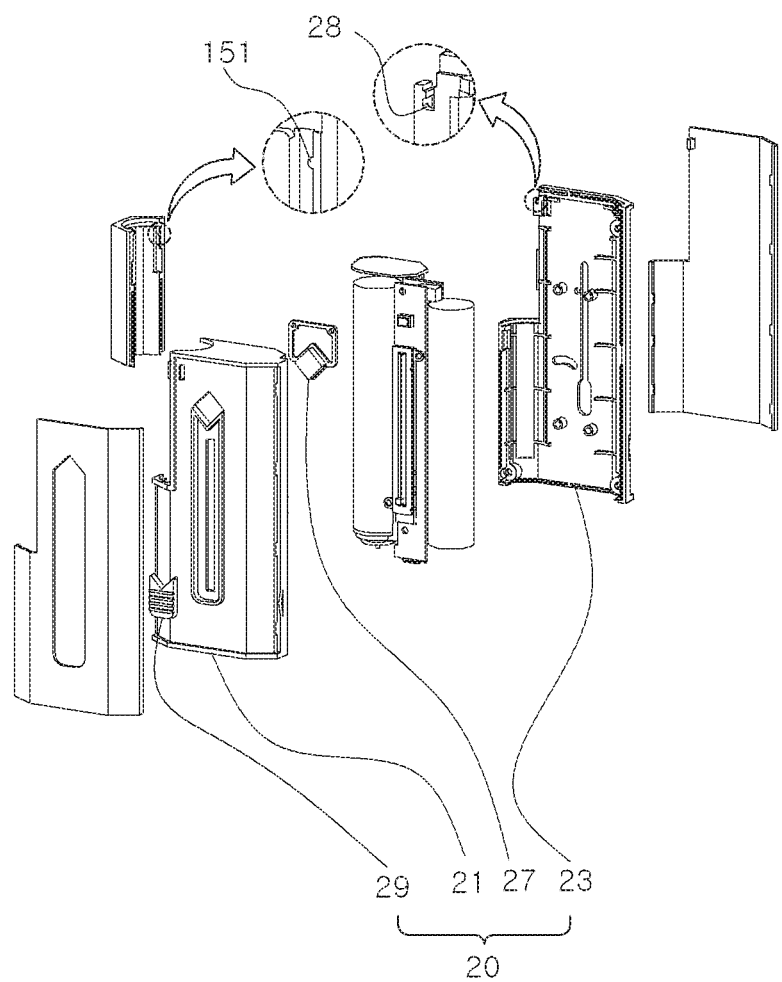
Figure 4:
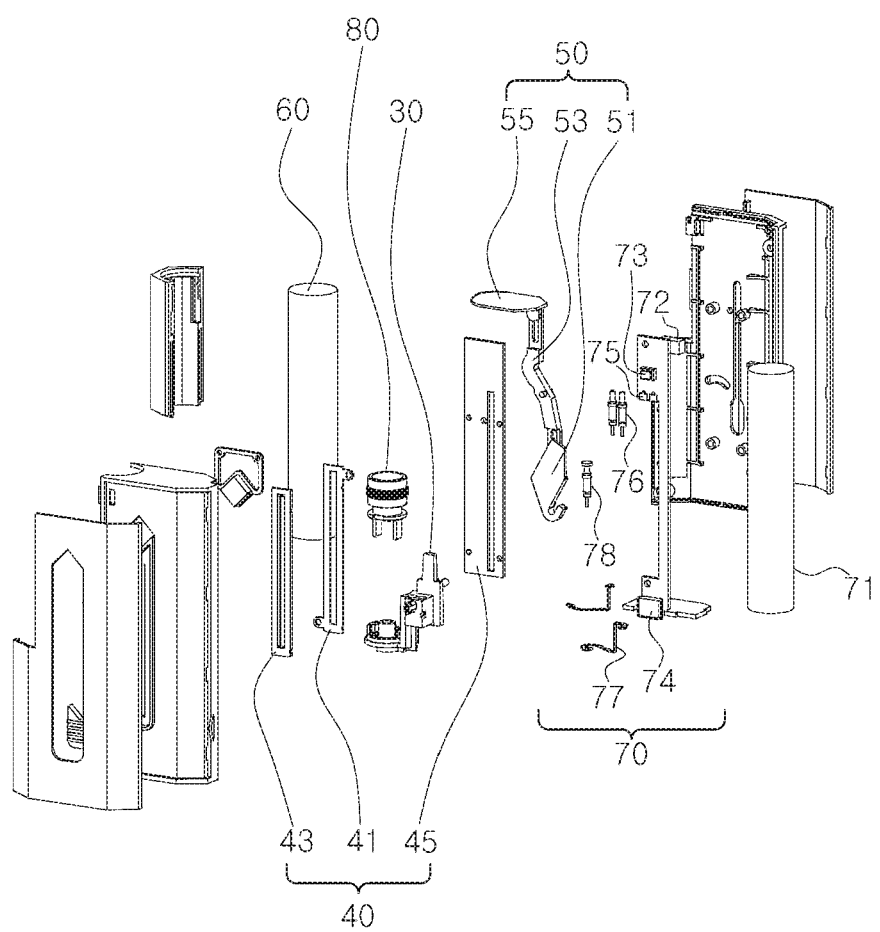
Figure 6A:
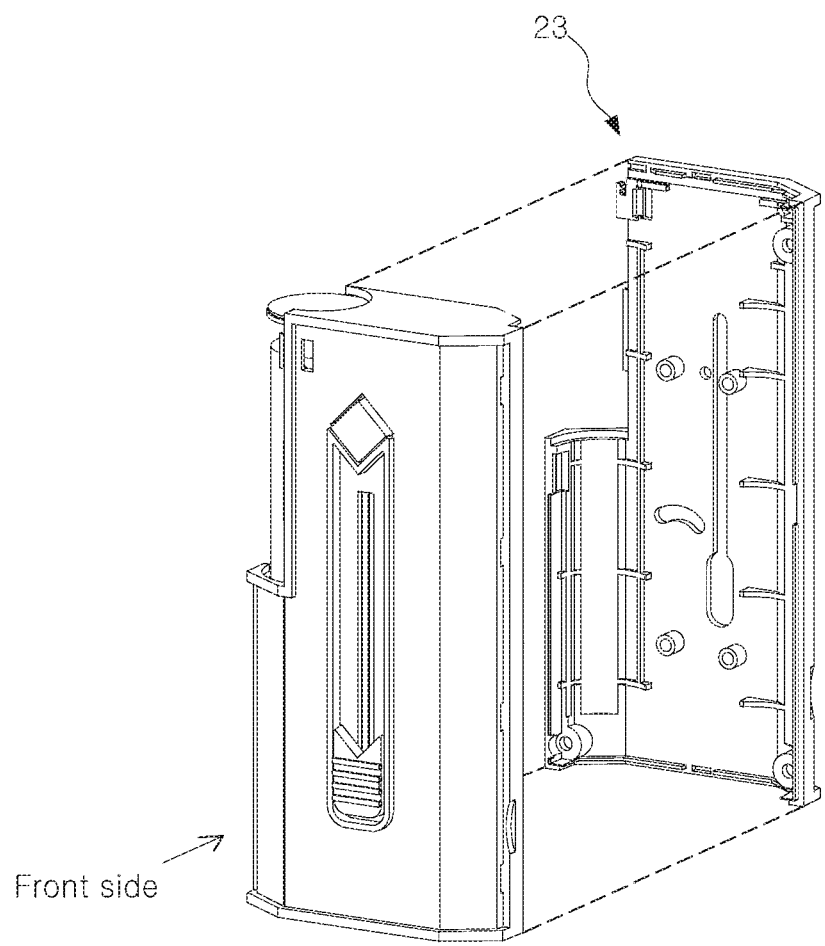
FIGS. 6a-6c shows perspective views of a rear-side casing.
Figure 6B:
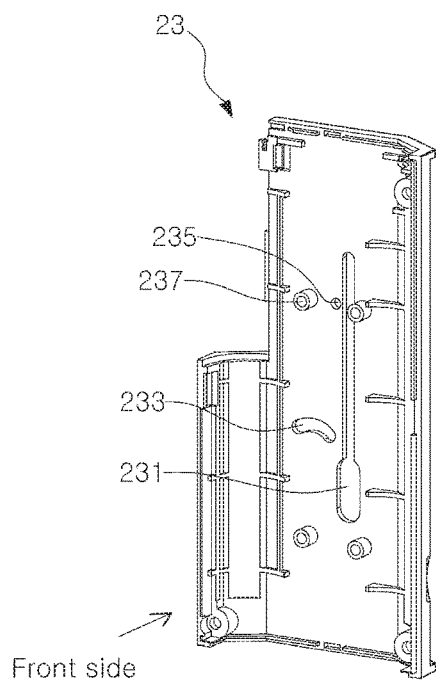
Figure 6C:
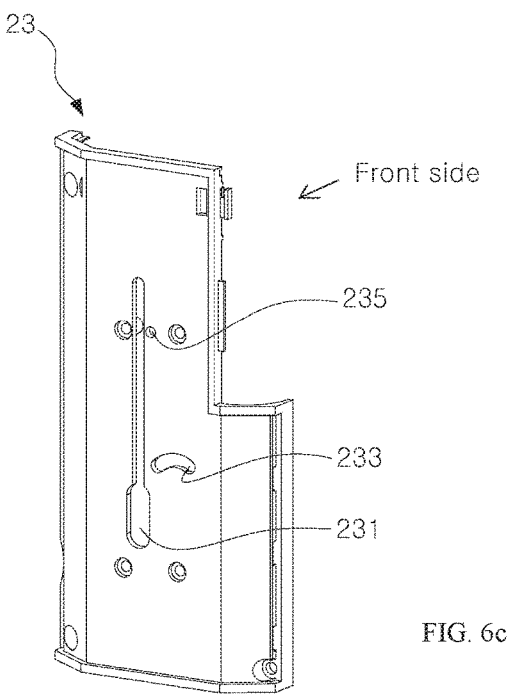
Figure 7A:
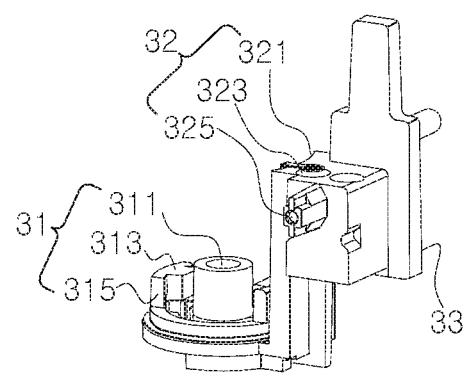
FIG. 7a is a front-side perspective view of, FIG. 7b is a rear-side perspective view of, and FIG. 7c is a top view of an elevating portion.
Figure 7B:
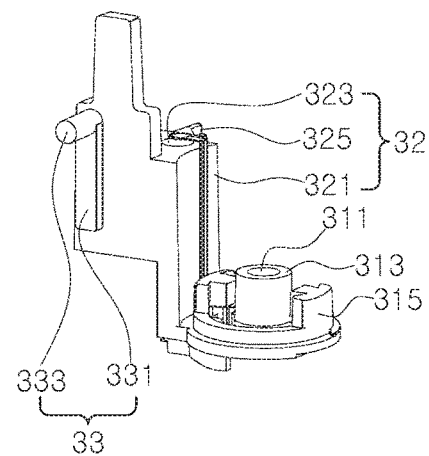
Figure 7C:
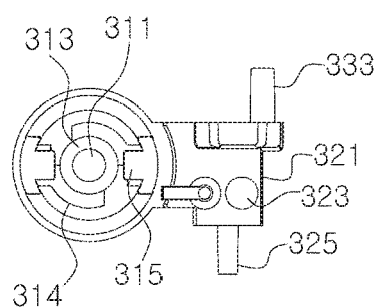
Figure 8A:
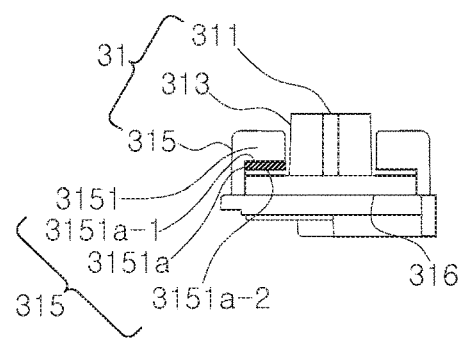
FIG. 8a is a front view of the elevating portion and a connector portion before coupling and FIG. 8b is a front view of the elevating portion and the connector portion after coupling.
Figure 8B:
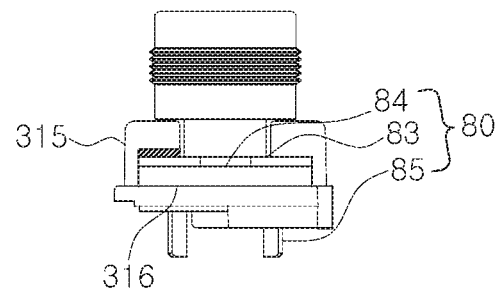
Figure 9A:
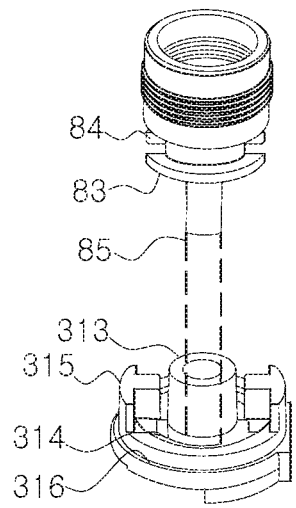
FIG. 9a is a perspective view of the elevating portion and the connector portion before coupling.
Figure 9B:
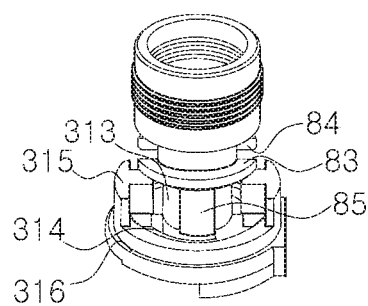
FIG. 9b is a perspective view of the elevating portion and the connector portion before insertion of a support coupling portion.
Figure 9C:
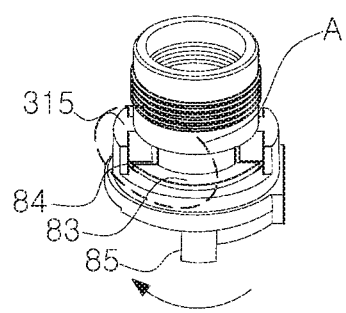
FIG. 9c is a perspective view of the elevating portion and the connector portion after insertion of the support coupling portion.
Figure 9D:
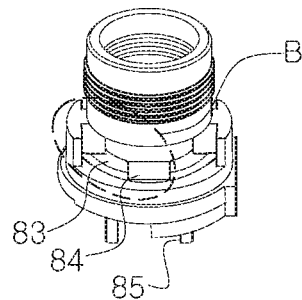
FIG. 9d is a perspective view of the elevating portion and the connector portion coupled by insertion and rotation of the connector portion.
Figure 10:
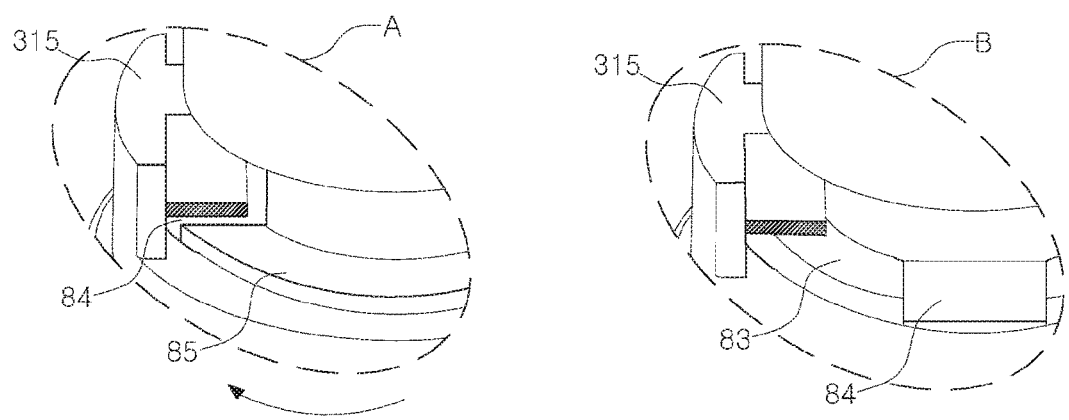
FIG. 10a is an enlarged view of "A" in FIG. 9
FIG. 10b is an enlarged view of "B" in FIG. 9.
Figure 11A:
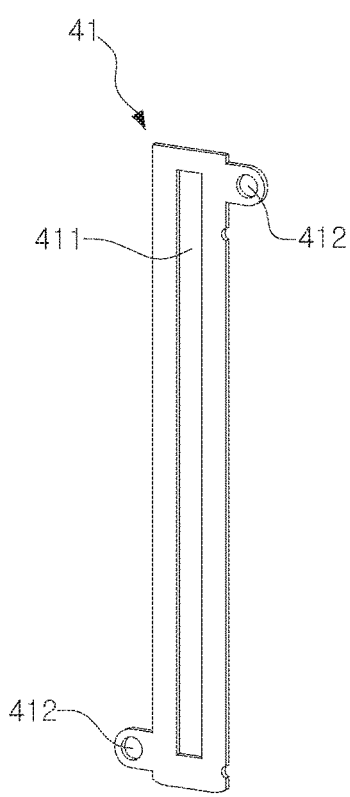
FIG. 11 is a front view of a fixing portion shown from the front side.
Figure 11B:
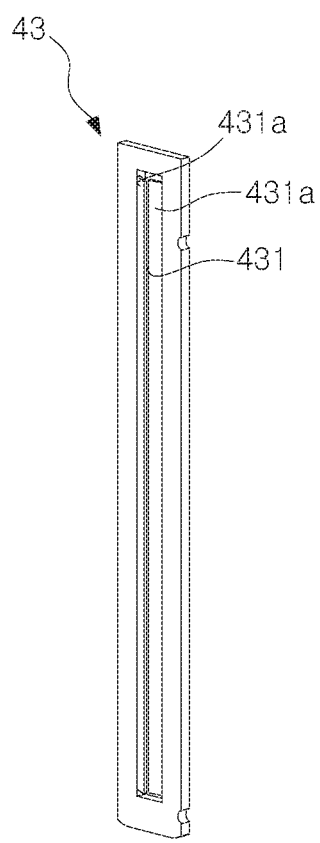
Figure 11C:
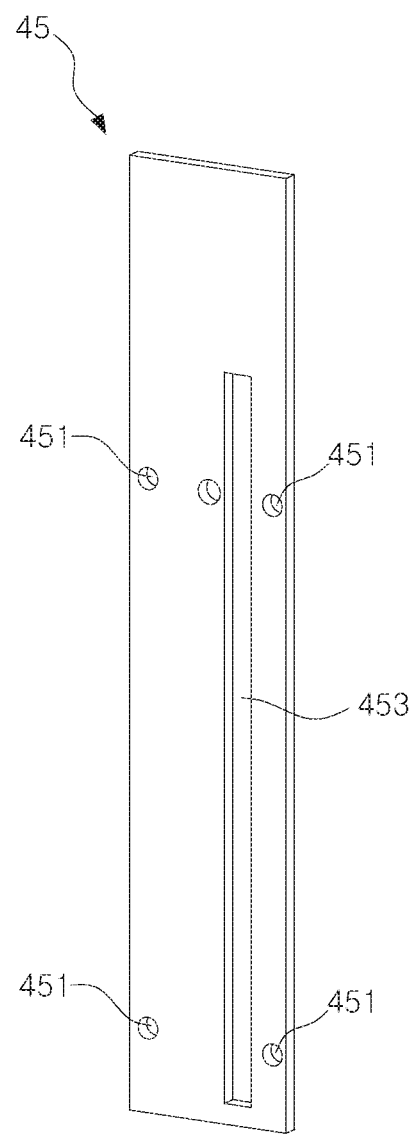
Figure 12A:
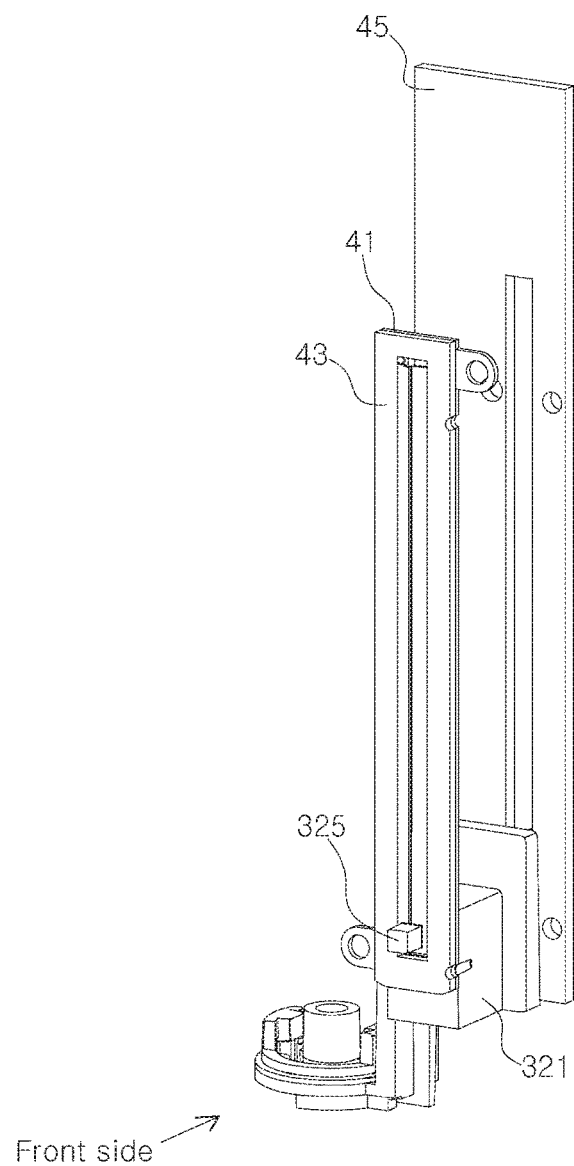
FIG. 12 is a perspective view showing a coupling structure of the elevating portion and the fixing portion shown from the front side.
Figure 12B:
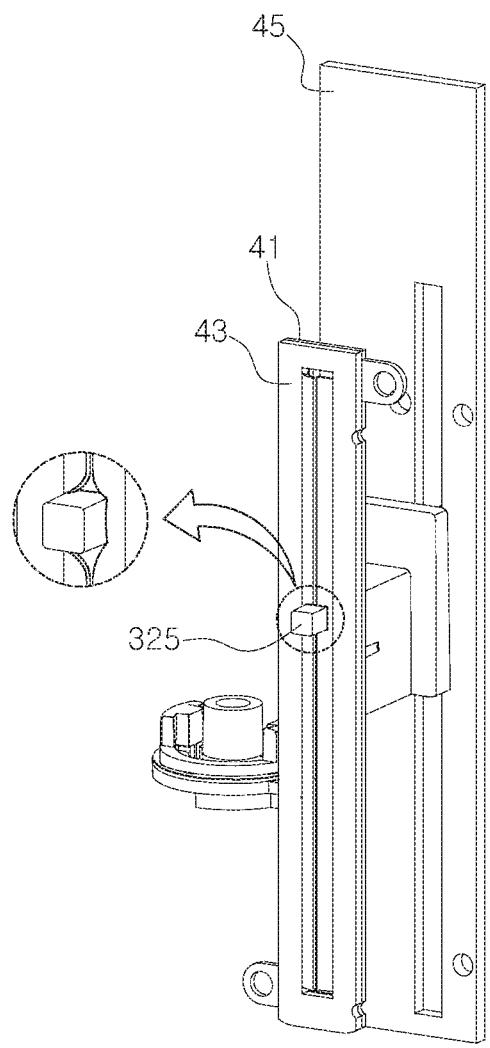
Figure 13A:
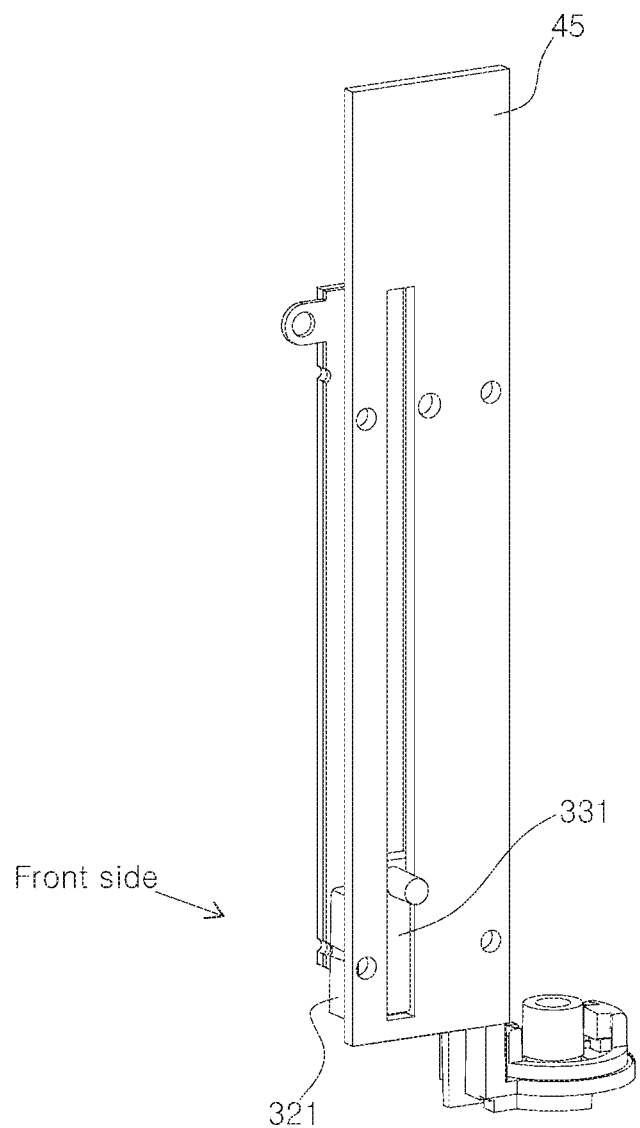
FIG. 13 is a perspective view showing the coupling structure of the elevating portion and the fixing portion shown from a rear side.
Figure 13B:
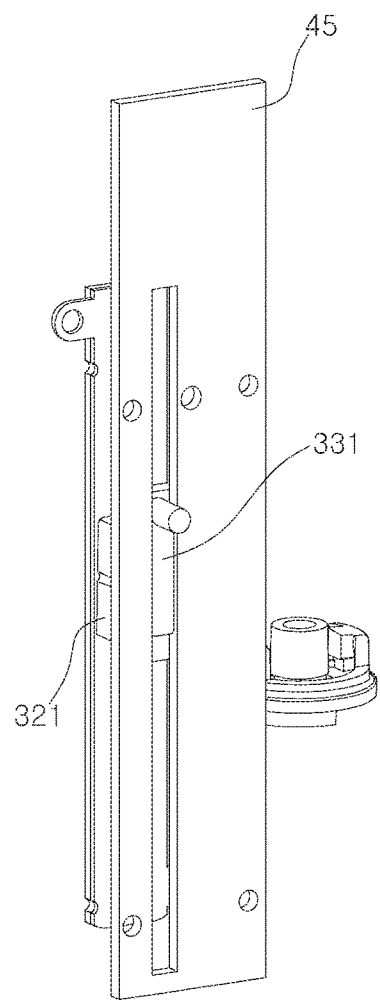
Figure 14A:
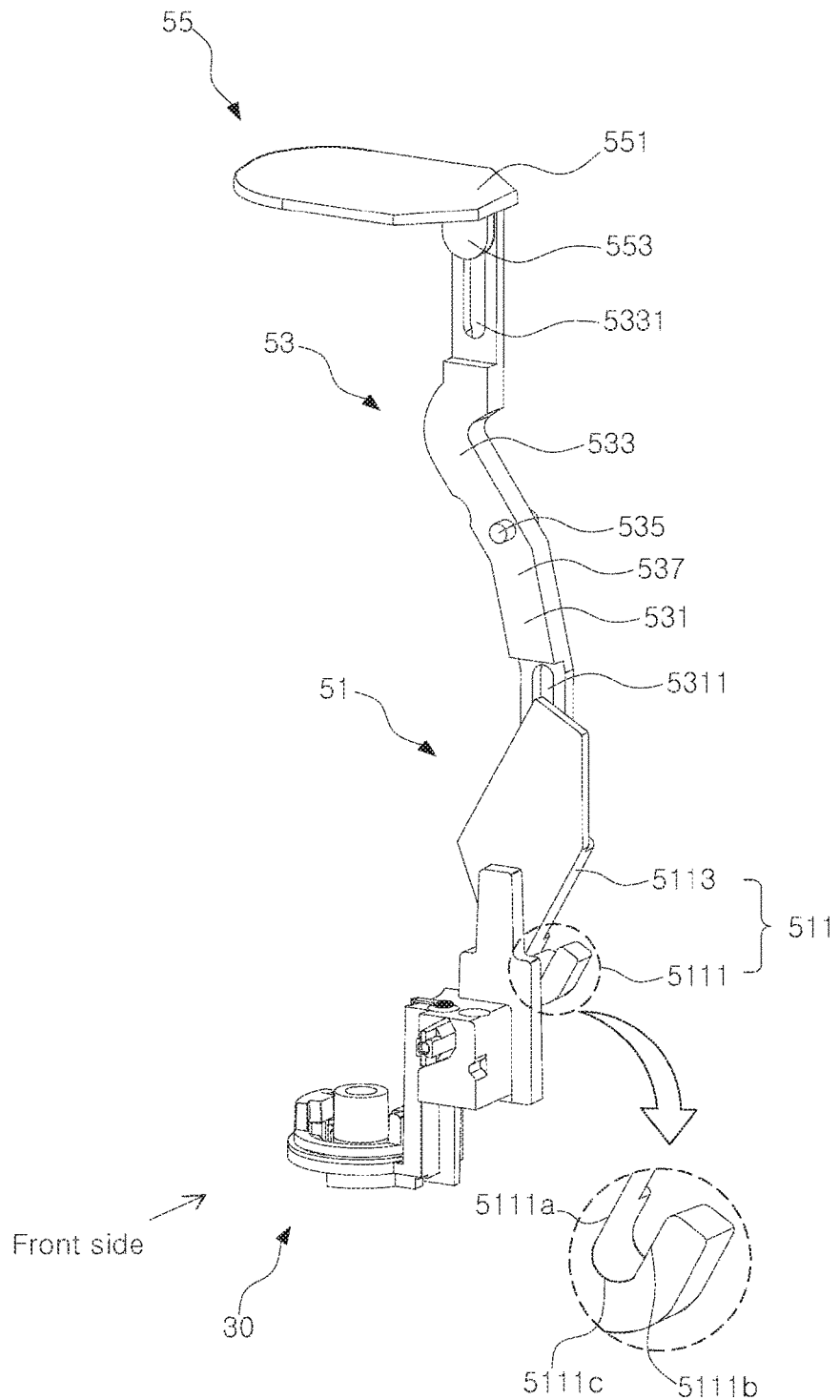
FIG. 14a is a front-side perspective view of and FIG. 14b is a rear-side perspective view of an opening and closing portion.
Figure 14B:
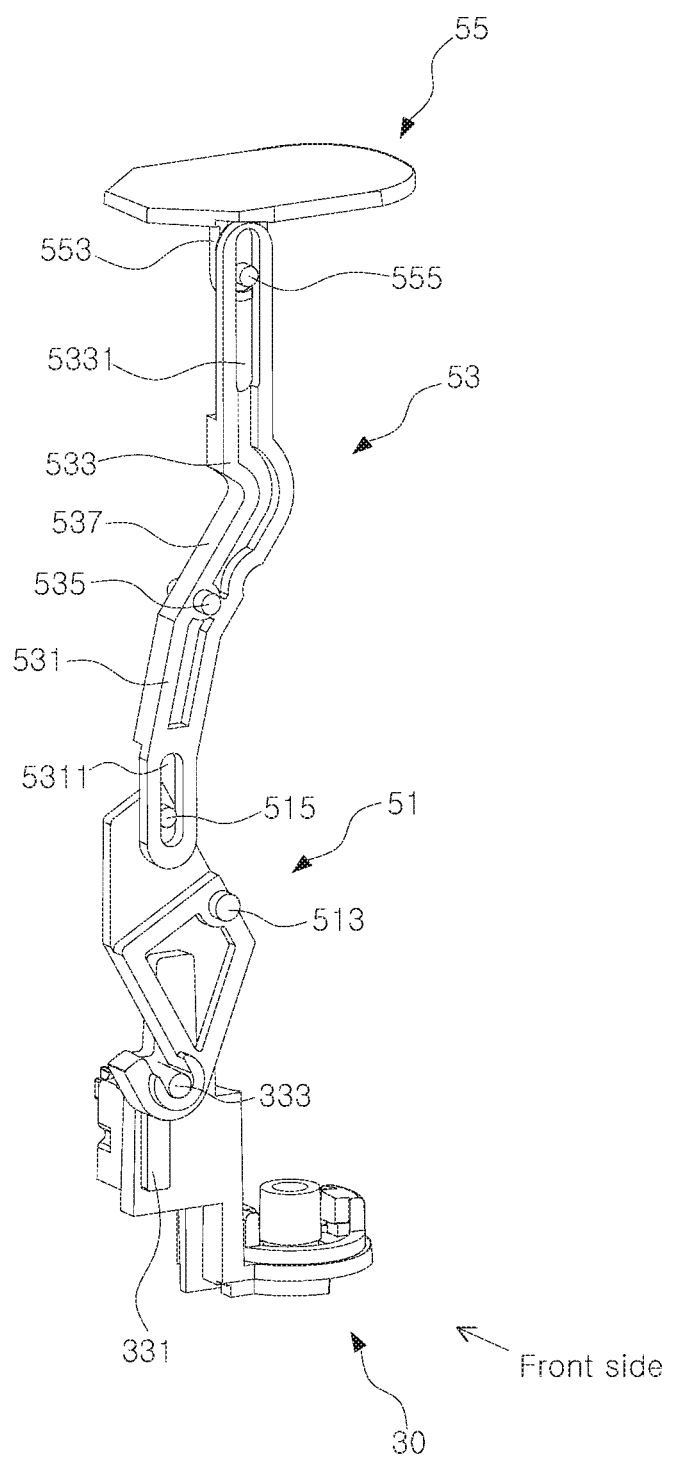
Figure 15A:
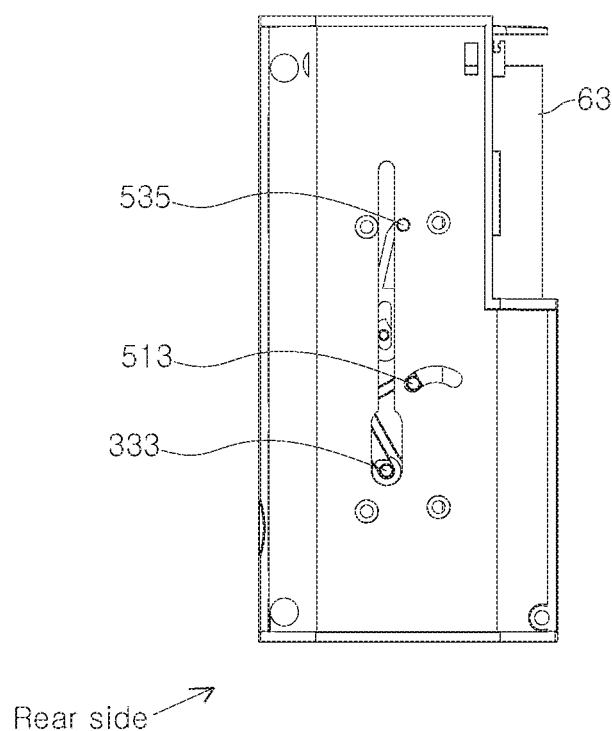
FIGS. 15 to 17 are reference views for describing operation of the electronic cigarette.
Figure 15B:
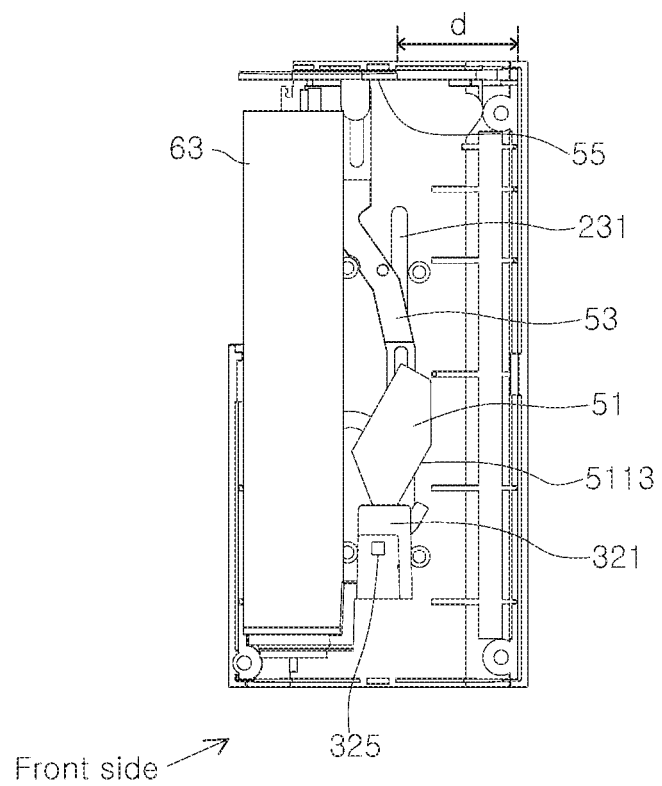
Figure 16A:
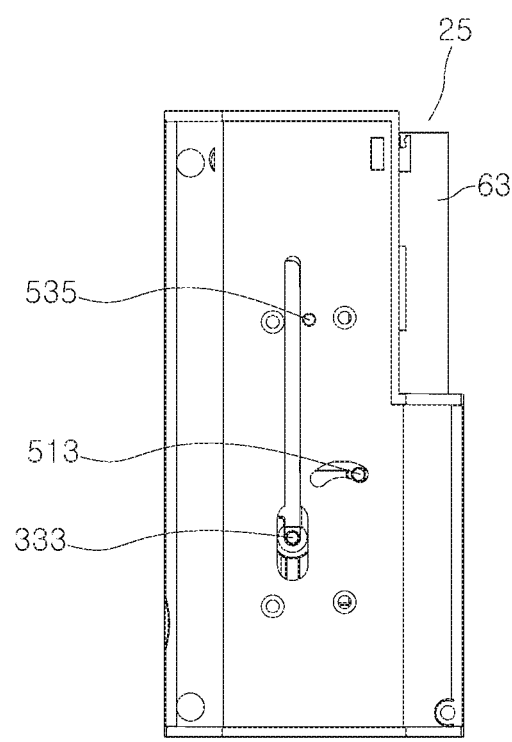
Figure 16B:
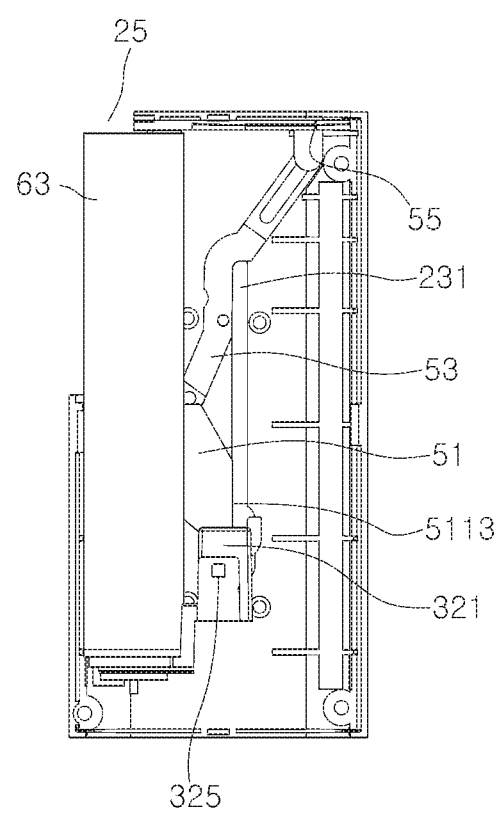
Figure 17A:
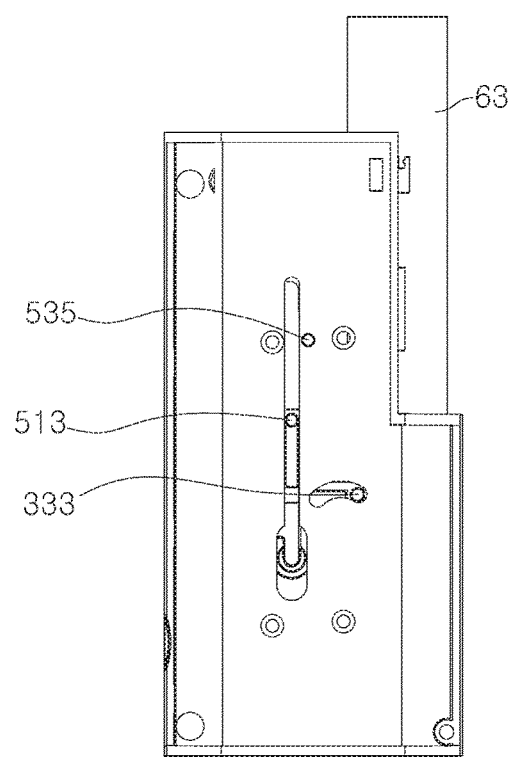
Figure 17B:
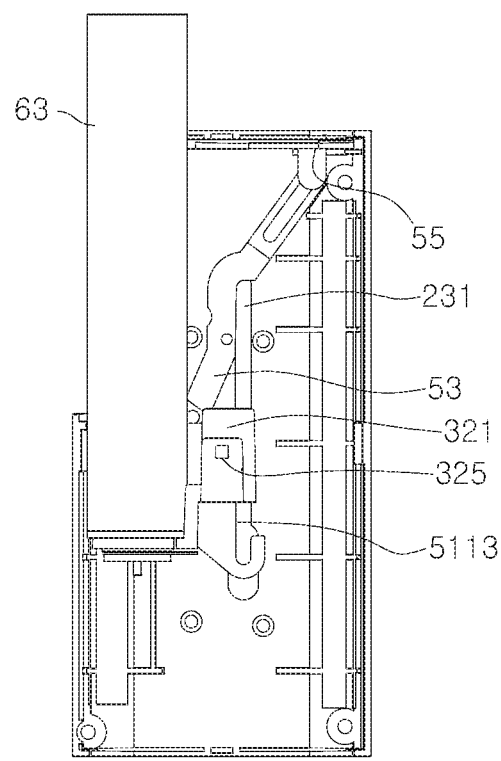
Figure 18:
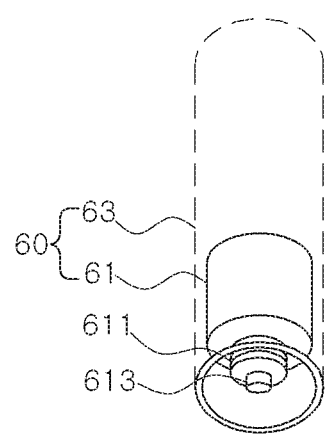
FIG. 18 is a perspective view of a smoke generating portion.
Figure 19:
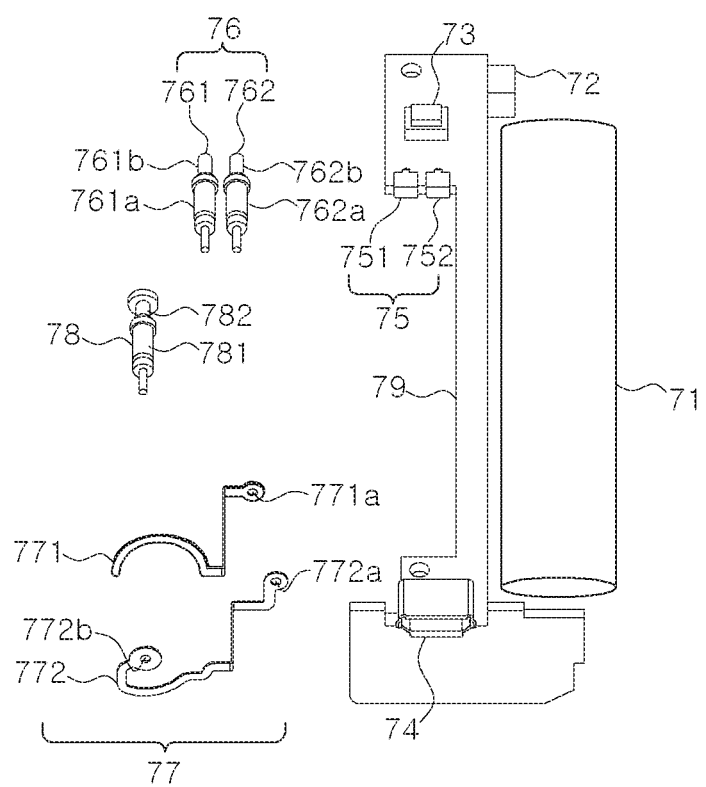
FIG. 19 is an exploded perspective view showing each element with respect to a power supply portion.
Figure 20A:
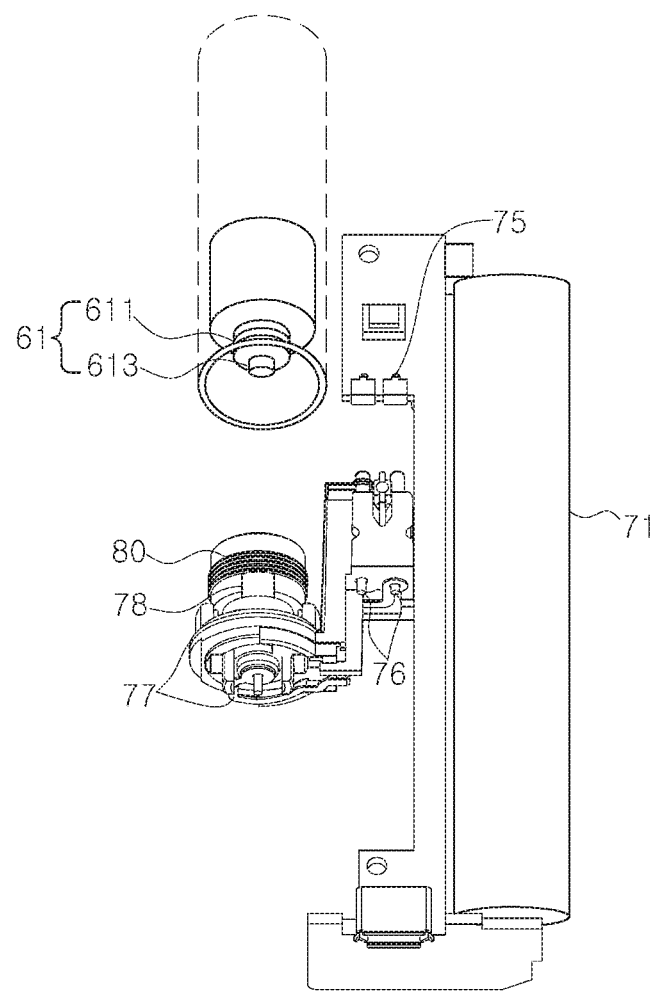
FIG. 20a is a perspective view of the smoke generating portion, the connector portion and the elevating portion with respect to the power supply portion before coupling
Figure 20B:
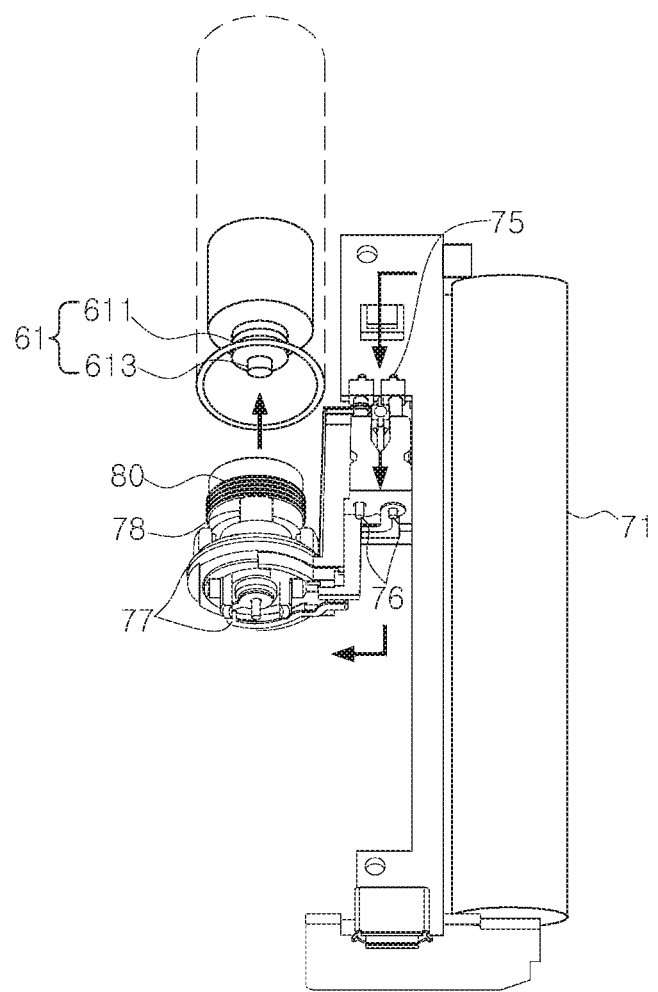
FIG. 20b is a perspective view of the smoke generating portion, the connector portion and the elevating portion with respect to the power supply portion after coupling.
Figure 21A:
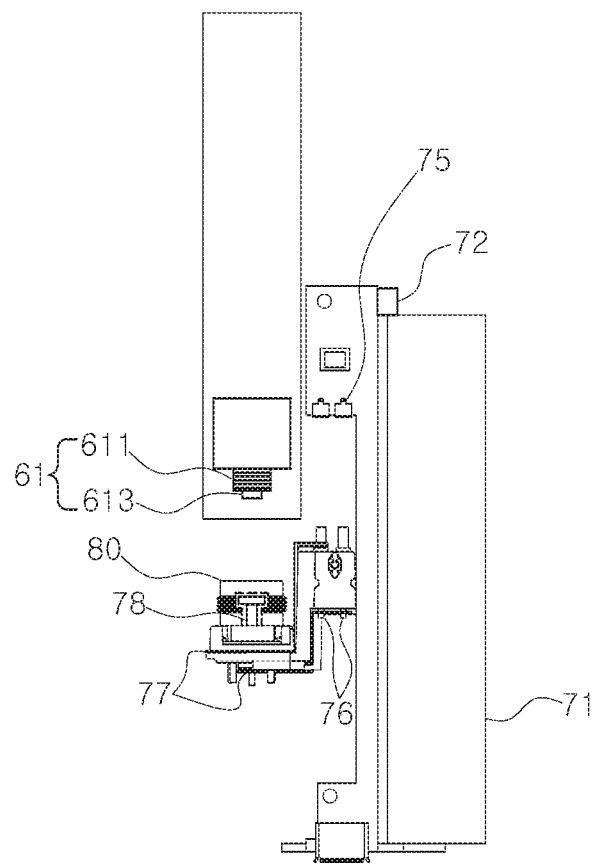
FIG. 21a is a perspective view of the smoke generating portion, the connector portion and the elevating portion with respect to the power supply portion before coupling
Figure 21B:
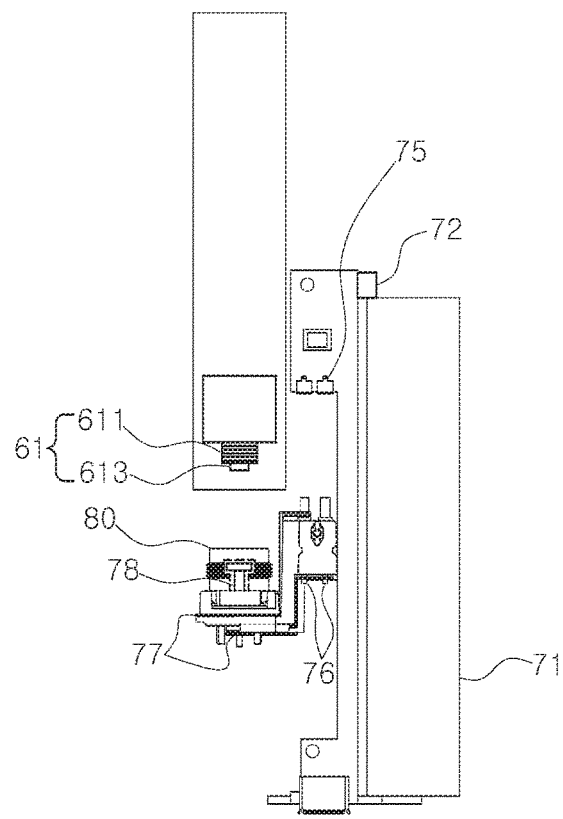
FIG. 21b is a perspective view of the smoke generating portion, the connector portion and the elevating portion with respect to the power supply portion after coupling.
Figure 22A:
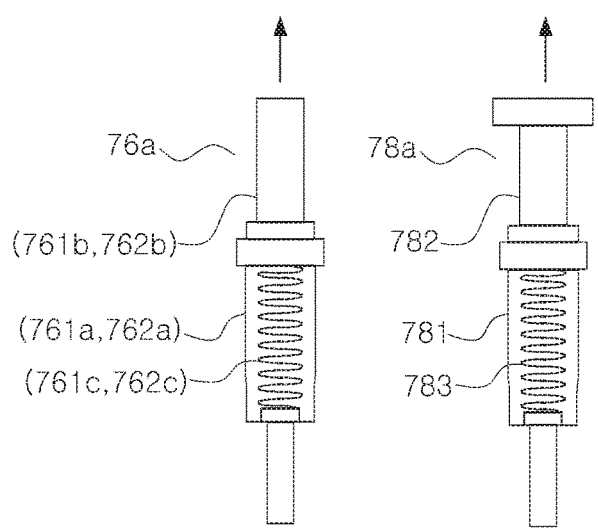
FIGS. 22a and 22b are sectional views of a stretched state and a shrunk state of a contact pin and a center pin when the contact pin and the center pin are pop-up type pins, including an elastic body inside.
Figure 22B:
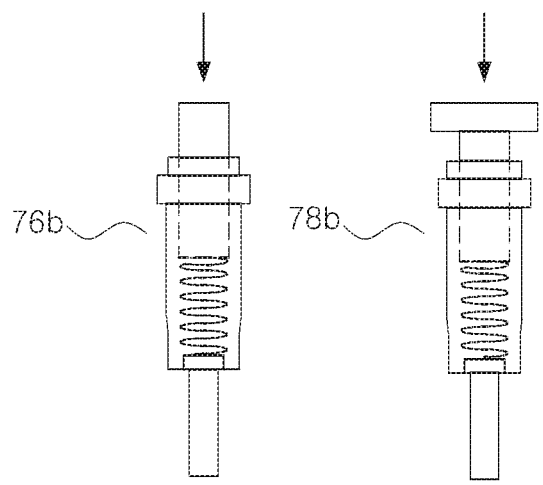
Figure 23A:
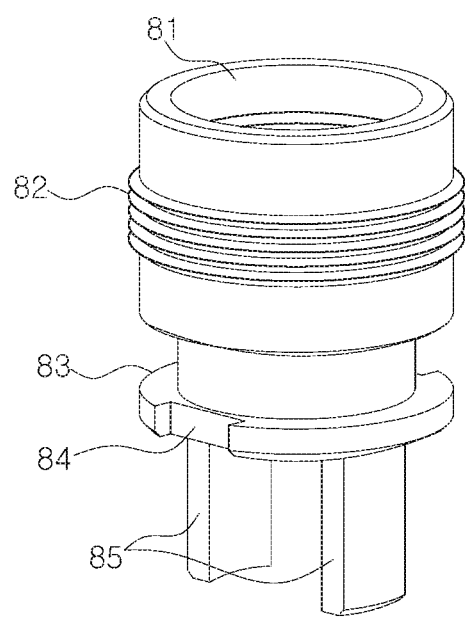
FIG. 23a is a perspective view of the connector portion and FIG. 23b is a perspective view showing a coupling relationship between the connector portion, the smoke generating portion and the elevating portion.
Figure 23B:
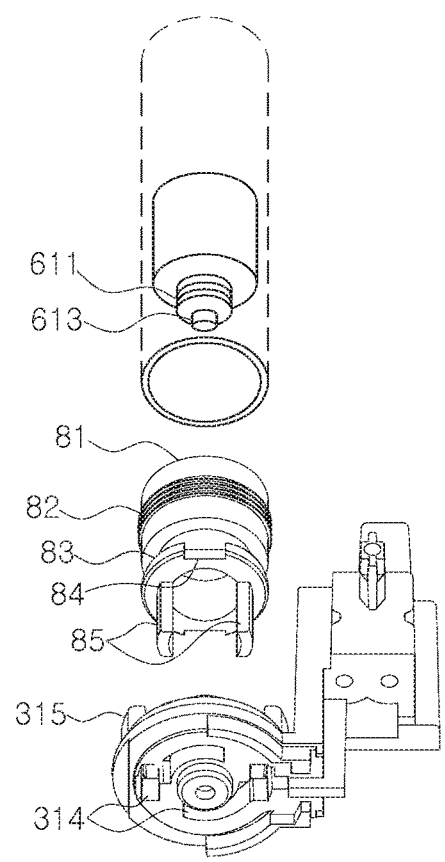
Figure 24:
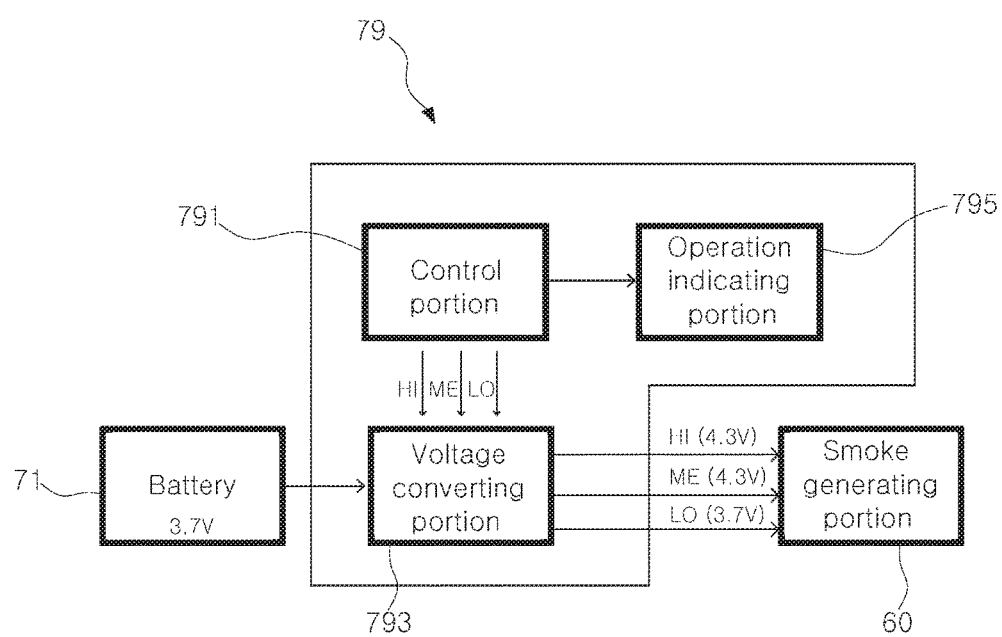
FIG. 24 is a block diagram which represents detailed elements of a main circuit board.
Figure 25:
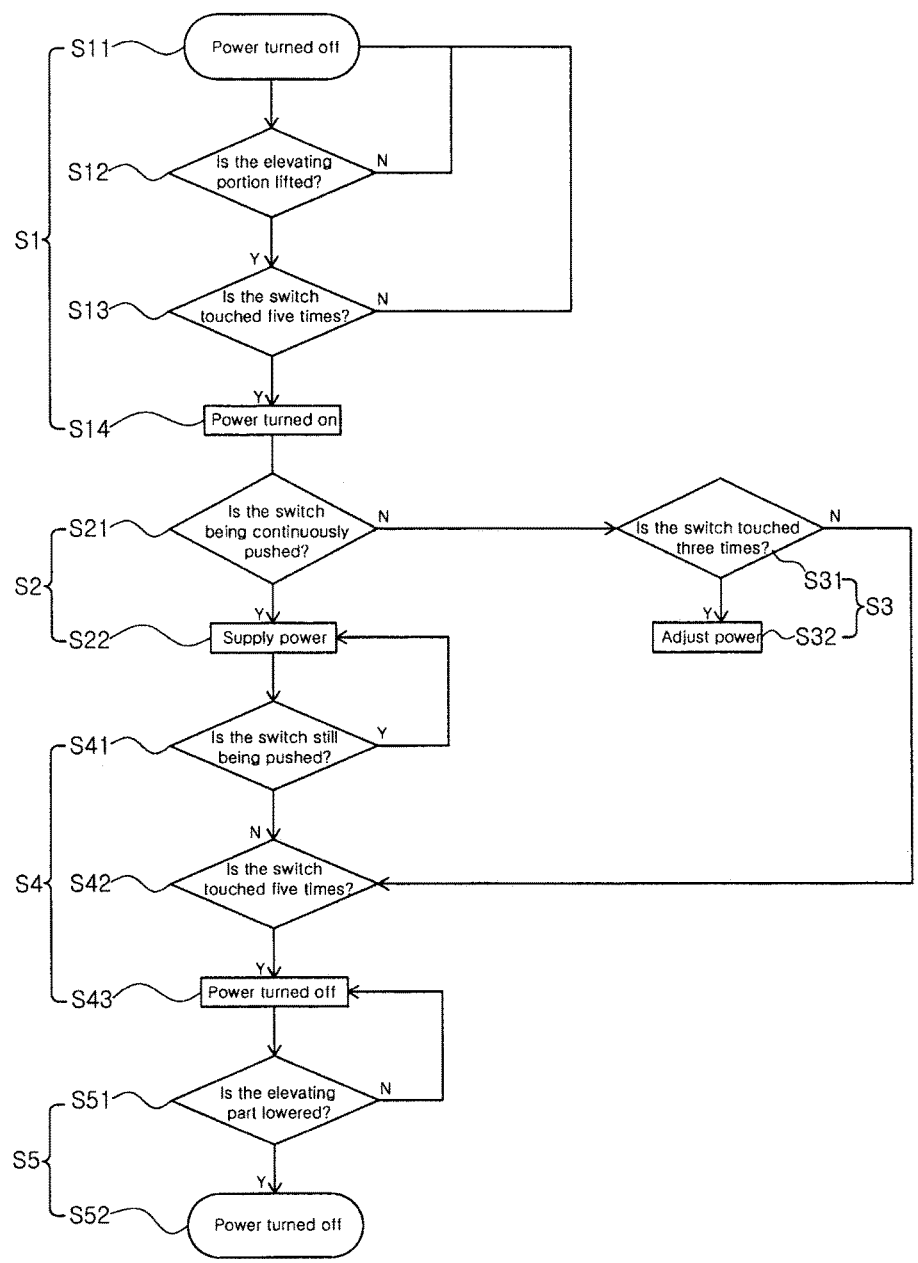
FIG. 25 is a flow chart for describing a method for turning on and off power or controlling a vaporization amount.

FIG. 1 is a perspective view of an electronic cigarette according to one embodiment of the present invention, shown from a front side; FIGS. 2 to 4 are exploded perspective views of each element of the electronic cigarette according to one embodiment of the present invention; FIG. 5 shows perspective views of a front-side casing; FIGS. 6a-6c show perspective views of a rear-side casing; FIG. 7a is a front-side perspective view of, FIG. 7b is a rear-side perspective view of, and FIG. 7c is a top view of an elevating portion; FIG. 8a is a front view of the elevating portion and a connector portion before coupling and FIG. 8b is a front view of the elevating portion and the connector portion after coupling (b); FIG. 9a is a perspective view of the elevating portion and the connector portion before coupling, FIG. 9b is a perspective view of the elevating portion and the connector portion before insertion of a support coupling portion, FIG. 9c is a perspective view of the elevating portion and the connector portion after insertion of the support coupling portion, and FIG. 9d is a perspective view of the elevating portion and the connector portion coupled by insertion and rotation of the connector portion; FIG. 10a is an enlarged view of "A" in FIG. 9 and FIG. 10b is an enlarged view of "B" in FIG. 9; FIG. 11 is a front view of a fixing portion shown from the front side; FIG. 12 is a perspective view showing a coupling structure of the elevating portion and the fixing portion shown from the front side; FIG. 13 is a perspective view showing the coupling structure of the elevating portion and the fixing portion shown from a rear side; FIG. 14a is a front-side perspective view of and FIG. 14b is a rear-side perspective view of an opening and closing portion; FIGS. 15 to 17 are reference views for describing operation of the electronic cigarette; FIG. 18 is a perspective view of a smoke generating portion; FIG. 19 is an exploded perspective view showing each element with respect to a power supply portion; FIG. 20a is a perspective view of the smoke generating portion, the connector portion and the elevating portion with respect to the power supply portion before coupling and FIG. 20b is a perspective view of the smoke generating portion, the connector portion and the elevating portion with respect to the power supply portion after coupling; FIG. 21a is a perspective view of the smoke generating portion, the connector portion and the elevating portion with respect to the power supply portion before coupling and FIG. 21b is a perspective view of the smoke generating portion, the connector portion and the elevating portion with respect to the power supply portion after coupling. FIGS. 22a and 22b are sectional views of a stretched state and a shrunk state of a contact pin and a center pin when the contact pin and the center pin are pop-up type pins, including an elastic body inside; FIG. 23a is a perspective view of the connector portion and FIG. 23b is a perspective view showing a coupling relationship between the connector portion, the smoke generating portion and the elevating portion; FIG. 24 is a block diagram which represents detailed elements of a main circuit board; and FIG. 25 is a flow chart for describing a method for turning on and off power or controlling a vaporization amount.

The electronic cigarette according to one embodiment of the present invention is described in reference to FIGS. 1 to 25. The electronic cigarette according to one embodiment of the present invention comprises: a casing portion 20 having an opening 25 and forming an outer shape of the electronic cigarette; a cover portion 10 formed to cover the outside of the casing portion 20; a smoke generating portion 60 (see FIG. 18) having an upper end protruding from the inside of the casing portion 20 to the outside of the casing portion 20 through the opening 25 and generating and discharging smoke by vaporizing a stored solution; an elevating portion 30 lifting or lowering the smoke generating portion 60; a fixing portion 40 keeping the elevating portion 30 from departing from a route when the elevating portion 30 is in the lifting or lowering motion; an opening and closing portion 50 operating in connection with the elevating portion 30 and opening or closing the opening 25; a power supply portion 70 which supplies power to the smoke generating portion 60; and a connector portion 80 which functions to connect between the smoke generating portion 60 and the elevating portion 30. According to the electronic cigarette of the present invention, power can be supplied to the inside without connecting wires, electric discharge is prevented and utilization efficiency is improved by being configured to supply or disconnect power by vertical motion of the elevating portion 30, and spilling a solution inside the smoke generating portion is prevented when a user holds and turns an upper region of the smoke generating portion 60 for separating the smoke generating portion 60.

Described is the connecting relationship between elements of the electronic cigarette. The electronic cigarette comprises: the outermost cover portion 10 as shown in FIG. 2, the casing portion 20 inside the cover portion 10 as shown in FIG. 3, the elevating portion 30, the fixing portion 40, the opening and closing portion 50, the smoke generating portion 60, the power supply portion 70, and the connector portion 80 inside the casing portion 20 as shown in FIG. 4.

As shown in FIG. 2, the cover portion 10, being a part formed to cover the outside of the casing portion 20, comprises: a front-side cover 11, a rear-side cover 13 and a cartridge cover 15.

The front-side cover 11, having a shape corresponding to the outer periphery of the front-side casing 21 viewed from the front side, includes a penetration groove 111 which penetrates a moving path of a control protrusion 325 such that the control protrusion 325 of the elevating portion 30 described below protrudes to the outside to move up and down.

The rear-side cover 13 has a shape corresponding to the outer periphery of the rear-side casing 23 when viewed from the rear side.

The front-side cover 11 and the rear-side cover 13 may be detachable from the front-side casing 21 and the rear-side casing 23, respectively, and preferably by a plurality of protrusions and grooves included in the outer peripheries of the front-side cover 11 and the rear-side cover 13, and the front-side casing 21 and the rear-side casing 23.

The cartridge cover 15, having a complementary shape to a cut out portion for exposing some upper part of the smoke generating portion 60 to the outside from the casing portion 20, is formed to cover the smoke generating portion 60. The cartridge cover 15 may be detachable from the casing portion 20, and preferably by attaching a groove 28 of the casing portion 20 to a protrusion 151 of the cartridge cover 15 as shown in FIG. 3. Accordingly, since the smoke generating portion 60 is exposed to the outside when the cartridge cover 15 is detached, a solution may be refilled in the smoke generating portion 60 without disassembling the casing portion 20.

The cover portion 10 protects internal components being inside the casing portion 20. In addition, the cover portion 10 being detachable from the casing portion 20 may be replaced with a cover having a design and, thus, can be used as a means to express individuality.

As shown in FIGS. 3 and 5, the casing portion 20 forms an outer shape of the electronic cigarette and includes the front-side casing 21, the rear-side casing 23, the opening 25, a switch button 27 and a control lever 29. A solution may easily be refilled in the smoke generating portion 60 without disassembling the casing portion 20 as a part of the casing portion 20 having a shape of an ellipsoidal cylinder is cut out to expose some upper part of the smoke generating portion 60.

Figure 5A:
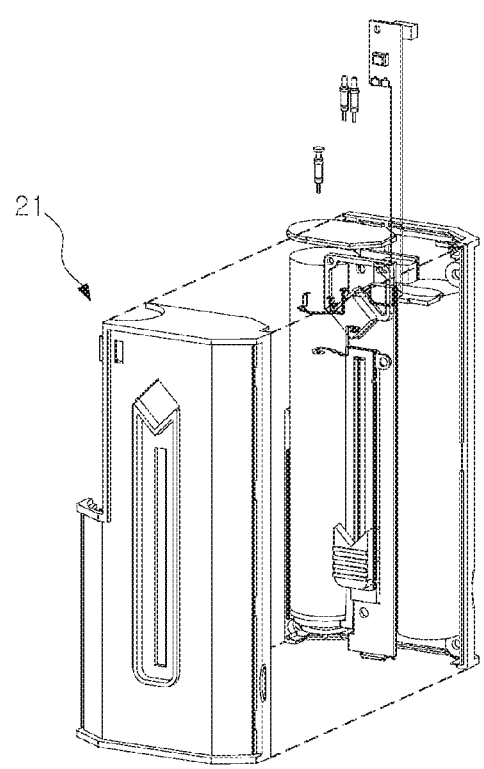
FIG. 5 shows perspective views of a front-side casing.
Figure 5B:
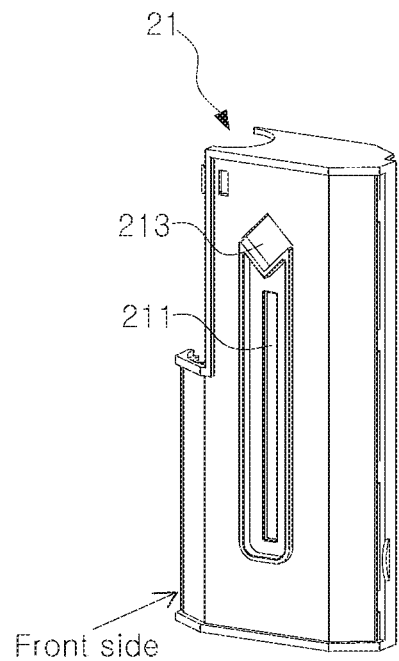
Figure 5C:
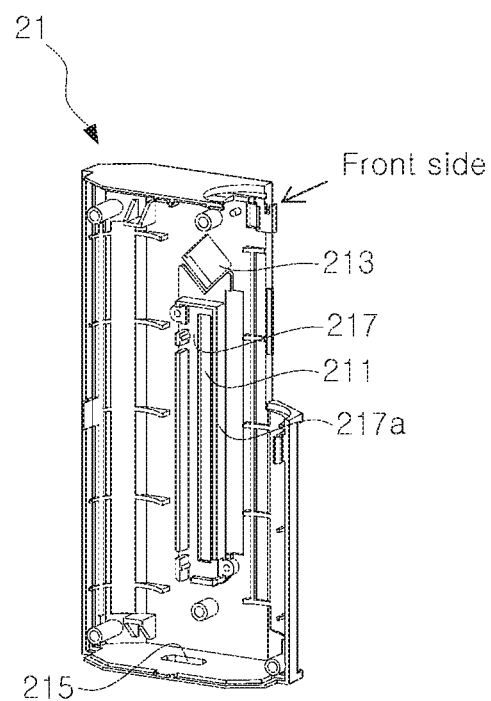

As shown in FIG. 5 (FIG. 5a is a perspective view of the front-side casing 21 separated from the rear-side casing 23, FIG. 5b is a perspective view of the front-side casing 21 viewed from a front side, and FIG. 5c is a perspective view of the front-side casing 21 viewed from a rear side), the front-side casing 21 forms the casing portion 20 by coupling to the rear-side casing 23 and includes a control protrusion groove 211, a switch groove 213, a charging terminal groove 215, and a fixing portion receiving groove 217.

The control protrusion groove 211 receives the control protrusion 325 of the elevating portion 30 by piercing the front-side casing 21 in a vertical direction.

The switch groove 213 is spaced at a certain interval apart from the control protrusion groove 211 and is formed to pierce the front-side casing 21. The switch groove 213 receives one end of a switch 73 of the power supply portion 70.

The charging terminal groove 215 is formed to penetrate a lower face of the front-side casing 21 and receives one end of a charging terminal 74 of the power supply portion 70.

The fixing portion receiving groove 217 is a space which receives a rubber member 43 of the fixing portion 40 and a control protrusion fixing piece 41. The fixing portion receiving groove 217 includes an area around the control protrusion groove 211, which is larger than the area of the control protrusion groove 211. The fixing portion receiving groove 217 is formed by a fixing portion receiving projection 217a protruded inward from the front-side casing 21 and, preferably, is a vertically extending rectangular space.

As shown in FIG. 6, (FIG. 6a is a perspective view of the rear-side casing 23 detached from the front-side casing 21, FIG. 6b is a perspective view of the rear-side casing 23 viewed from the front side, and FIG. 6c is a perspective view of the rear-side casing 23 viewed from the rear side.) the rear-side casing 23 forms the casing portion 20 by coupling to the front-side casing 21 and includes a bent protrusion groove 231, a rotation guide protrusion groove 233, a rotation axis protrusion groove 235 and a fixing protrusion 237.

The bent protrusion groove 231 pierces the rear-side casing 23 in the vertical direction and receives a bent protrusion 333 of the elevating portion 30.

The rotation guide protrusion groove 233 as a curved shape pierces the rear-side casing 23 and is disposed at a certain interval from the bent protrusion groove 231 and receives a rotation guide protrusion 515 of the opening and closing portion 50.

The rotation axis protrusion groove 235 pierces the rear-side casing 23 at a certain interval from the bent protrusion groove 231 and fixes a rotation axis protrusion 535 of the opening and closing portion 50.

The fixing protrusion 237 protrudes inward from the rear-side casing 23 and is coupled to a guide protrusion fixing piece 45 of the fixing portion 40.

As shown in FIG. 1, the opening 25 is formed as a cut-out having a complementary shape to the shape of the cross section of the cartridge 63 of the smoke generating portion 60 when the front-side casing 21, the rear-side casing 23 and the cartridge cover 15 are coupled. The opening 25 becomes a moving path of the smoke generating portion 60 as the opening 25 remains closed when the smoke generating portion 60 is inside the casing portion 20 and the opening 25 is opened when the smoke generating portion 60 is lifted to the outside of the casing portion 20.

As shown in FIG. 3, a switch button 27 is disposed between the switch 73 of the power supply portion 70 and the front-side casing 21 to have a shape of covering the switch 73 and the user may press the switch 73 by pressing the switch button 27.

The control lever 29 receives the control protrusion 325 when the control protrusion 325 of the elevating portion 30 is protruded to the outside through the control protrusion groove 211 of the front-side casing 21, thereby allowing the user to move the elevating portion 30 by operating the control lever 29.

As shown in FIG. 4 and FIGS. 7 to 10, the elevating portion 30 is disposed inside the casing portion 20 to lift and lower the smoke generating portion 60 and includes a support 31, an elevating body portion 32, and a guide portion 33.

The support 31 is an element which supports a lower end of the smoke generating portion 60. The support 31 may preferably have a shape corresponding to the cross-sectional area of the cartridge 63 of the smoke generating portion 60 but may have any shape if the smoke generating portion 60 is stably supported and lifted and lowered. The support 31 includes a center pin coupling portion 311, a connector coupling portion 313, a connector insertion groove 314, and a connector fixing portion 315.

The center pin coupling portion 311 is a hole of a certain size, formed to penetrate from an upper side to the lower side inside the connector coupling portion 313. The center pin coupling portion 311 is a part capable of coupling to the center pin 78 of the power supply portion 70 by insertion as described below, which enables the center pin 78 coupled to the elevating portion 30 to move up and down integrally with the elevating portion 30.

The connector coupling portion 313 is a part formed by protruding upward from an upper center part of the support 31. The connector portion 80 can be coupled by insertion to the outside of the connector coupling portion 313, and the center pin 78 can be coupled by insertion to the center pin coupling portion 311 formed inside of the connector coupling portion 313.

The connector insertion groove 314 is a part shaded in FIGS. 7c and 9, in which a support coupling portion 85 of the connector portion 80 described below can be inserted at a circumference of the connector coupling portion 313. Accordingly, the connector insertion groove 314 fixes the connector portion 80 coupled to the support 31 not to move in the horizontal direction.

The connector fixing portion 315 includes a protrusion 3151 formed upward at an upper periphery of the support 31. The protrusion 3151 has an inclined surface 3151a inclined in a circumferential direction at the lower end to fix the support 31 coupled to the connector portion 80 not to move in the vertical direction.

In addition, a part of the connector fixing portion 315 is formed to protrude toward a center part of the support 31 on a plane, which allows the connector fixing portion 315 to be engaged inside a support insertion groove 84 of the connector portion 80 in the horizontal direction described below and be coupled in the vertical direction by insertion, thereby facilitating coupling of the connector portion 80 and the support 31.

Also, the inclined surface 3151a has one end 3151a-1 of the inclined surface having a smaller height than the other end 3151a-2 of the inclined surface. If the connector portion 80 is inserted in the support 31 and rotated, the support insertion portion 83 proceeds to the other end 3151a-2 of the inclined surface through the one end 3151a-1 of the inclined surface. While proceeding to the other end 3151a-2, the support insertion portion 83 is easily inserted in the other end 3151a-2 of the inclined surface and pressed by the other end 3151a-2 of the inclined surface, which fixes the connector portion 80 firmly fixed in the support 31 not to move in the horizontal direction.

Meanwhile, it is common to use the same method of coupling, such as screw connection, for coupling the smoke generating portion 60 and the connector portion 80, and the connector portion 80 and the elevating portion 30, in the electronic cigarette according to prior art. In such cases, when the user holds and turns an upper region of the smoke generating portion 60 for separating the smoke generating portion 60, the connection between the smoke generating portion 60 and the connector portion 80 may sometimes be released before the connection between the connector portion 80 and the elevating portion 30, which causes the solution stored in the smoke generating portion 60 to be spilled.

However, the electronic cigarette according to the present invention is easily configured to have lesser coupling force in horizontal direction rotation, compared to screw connection, since the protrusion 3151 of the connector fixing portion 315 fixes the connector portion 80 in fixing the coupling between the connector portion 80 and the elevating portion 30. Accordingly, when the user holds and turns the upper region of the smoke generating portion 60 for separating the smoke generating portion 60, the connection between the connector portion 80 and the elevating portion 30 is released before the connection between the smoke generating portion 60 and the connector portion 80, thereby preventing the solution in the smoke generating portion 60 from being spilled.

The elevating body portion 32 is lifted or lowered by control of the user to lift or lower the smoke generating portion 60 and includes an elevating body 321, a contact pin coupling portion 323, and the control protrusion 325.

The elevating body 321 is a portion formed as a hexahedral shape at one side of the support 31. The control protrusion 325 protrudes toward the front side in the elevating body 321.

The contact pin coupling portion 323 forms a hole of a certain size, which penetrates from an upper side to a lower side of the elevating body 321 and can be coupled to the contact pin 76 of the power supply portion 70 by insertion, described below. Hence, the contact pin 76 is capable of moving up and down while being coupled to the elevating portion 30, which improves stability and durability in continuous use for a long period of time due to stronger power connection compared to a prior method where power is supplied by connecting the power supply terminal 75 to the elevating portion 30 by a wire.

The control protrusion 325 has a certain length exposed to the outside of the casing portion 20 by passing through the control protrusion groove 211 of the front-side casing 21, the certain length being coupled to the control lever 29 and allows the vertical movement of the elevating portion 30 to be controlled.

The guide portion 33 is formed in a rear side of the elevating body 321, guides lifting and lowering of the elevating body portion 32, and includes a guide protrusion 331 and the bent protrusion 333.

The guide protrusion 331 is formed vertically and protruded in the rear side of the elevating body 321. The guide protrusion 331 received in the guide protrusion fixing piece 45 of the fixing portion 40 keeps the elevating portion 30 from departing from the moving path.

The bent protrusion 333 is bent and extends at an upper end of the guide protrusion 331. The bent protrusion 333 is connected to the opening and closing portion 50 and rotates the opening and closing portion 50 when the elevating portion 30 ascends or descends.

A coupling relationship between the elevating portion 30 and the connector portion 80 will be described in detail below with reference to FIGS. 9 and 10. Also, parts which may be difficult to observe in the perspective views, i.e., the support insertion groove 84 in FIG. 9 and the support insertion portion 83 in FIG. 10 are shaded for simpler description.

As shown in FIG. 9a, the elevating portion 30 is coupled to the connector portion 80 by inserting a lower end of the connector portion 80 in an upper end of the support 31 of the elevating portion 30. More specifically, the connector portion 80 is rotated in the horizontal direction such that the connector fixing portion 315 and the support insertion groove 84 engage with each other on a plane for insertion in the vertical direction.

As shown in FIG. 9b, the support coupling portion 85 is inserted in the connector insertion groove 314 while the connector portion 80 is in the rotated state.

As shown in FIGS. 9c and 10a, when the support coupling portion 85 is completely inserted and mounted inside the connector insertion groove 314, As shown in FIGS. 9d and 10b, the connector portion 80 may move in the vertical direction if the connector fixing portion 315 and the support insertion groove 84 keep engaged in the horizontal direction. To prevent this, the connector portion 80 is rotated again in the horizontal direction to fix the coupling between the support 31 and the connector portion 80 in the vertical direction.

The electronic cigarette may not normally operate if the elevating portion 30 which moves up and down inside the casing portion 20 departs from its moving path. Thus, according to the present invention, the fixing portion 40 fixed in the casing portion 20 is configured to receive the elevating portion 30 such that the elevating portion 30 does not depart from its moving path.

As shown in FIG. 4 and FIGS. 11 to 13, the fixing portion 40 is an element which receives the elevating portion 30 and includes the control protrusion fixing piece 41, the rubber member 43, and the guide protrusion fixing piece 45.

The control protrusion fixing piece 41 is received in the fixing portion receiving groove 217 of the front-side casing 21 and fixed inside the casing portion 20. Having a shape corresponding to an inner periphery face of the fixing portion receiving groove 217, the control protrusion fixing piece 41 includes a control protrusion receiving groove 411 formed vertically by penetrating the moving path of the control protrusion 325 to receive the control protrusion 325, thereby preventing the elevating portion 30 from departing from a defined moving path.

The control protrusion fixing piece 41 includes a protrusion 412 extending in an upper side and/or a lower side toward a left side and/or a right side. Thus, the control protrusion fixing piece 41 may easily be detached from the fixing portion receiving groove 217 by raising the protrusion 412.

The rubber member 43 disposed in a front side of the control protrusion fixing piece 41 is received in the fixing portion receiving groove 217, has a shape corresponding to an inner periphery face of the fixing portion receiving groove 217, and completely covers the control protrusion groove 211 of the front-side casing 21 to prevent foreign materials from entering the inside of the casing portion 20.

Also, the rubber member 43 includes a gap 431 in a vertical direction on the moving path of the control protrusion 325, through which the control protrusion 325 protrudes to the outside. Since the gap 431 is formed by a pair of wings 431a protruded by a certain angle toward a front direction, it is easy for the control protrusion 325 to protrude to the outside through the gap 431.

The wings 431a having elasticity apply pressure to the sides of the control protrusion 325 to prevent the control protrusion 325 from shaking during the vertical motion, and fixes the control protrusion 325 to be positioned in a center of the control protrusion groove 211 of the front-side casing 21, thereby facilitating ascending and descending movement of the elevating portion 30.

The guide protrusion fixing piece 45 preferably has a rectangular shape extending in the vertical direction and is fixed inside the casing portion 20 by including the fixing protrusion receiving groove 451 and coupling to the fixing protrusion 237 of the rear-side casing 23. Moreover, the guide protrusion fixing piece 45 includes the guide protrusion receiving groove 453 formed vertically and penetrating the moving path of the guide protrusion 331 of the elevating portion 30 and receives the guide protrusion 331 such that the elevating portion 30 does not depart from the defined moving path.

Described below is the coupling relationship between the elevating portion 30 and the fixing portion 40.

As shown in FIG. 12, the control protrusion 325 ascends or descends while protruding to the outside through the control protrusion fixing piece 41 and the rubber member 43. As shown in FIG. 13, since the guide protrusion 331 is received in the guide protrusion fixing piece 45 during ascent and descent, the elevating portion 30 does not depart from the defined moving path.

When the elevating portion 30 is controlled to raise or lower the smoke generating portion 60, the opening 25 is opened in connection with the opening and closing portion 50, which will be described in detail below.

As shown in FIG. 4 and FIGS. 14 to 17 (FIG. 14a is a perspective view of the opening and closing portion 50 viewed from the front side, and FIG. 14b is a perspective view of the opening and closing portion viewed from the rear side. Also, in FIG. 14, the guide protrusion fixing piece 45 disposed between the elevating portion 30 and the opening and closing portion 50 is omitted for convenience). The opening and closing portion 50 operates in connection with the elevating portion 30 and corresponds to an element which opens or closes the opening 25. The opening and closing portion 50 includes a moving member 51, a connecting member 53 and a door 55.

The moving member 51 having an upper end coupled to the connecting member 53 and a lower end contacting with the bent protrusion 333 rotates in connection with the ascent and descent of the elevating portion 30 and opens or closes the opening 25 by changing a location of the connecting member 53 and the door 55. The moving member 51 includes a ring portion 511, a rotation guide protrusion 515 and a connecting protrusion 513.

Because the moving member 51 preferably has a rhomboidal shape, spaces enough to include the guide protrusion 515, the connecting protrusion 513 and the like can be obtained compared to the moving member having a rectangular shape. Also, more smooth rotation is accomplished in a small space inside the casing portion 20 compared to the moving member having a square shape.

The ring portion 511 has a J-shaped hook shape by one long surface and the other short surface, is formed by bending in a lower end of the moving member 51, and includes a ring groove 5111 and an extending inclined surface 5113.

The ring groove 5111 is depressed in a distal end of the ring portion 511 and receives the bent protrusion 333. The ring groove 5111 includes a first inclined surface 5111a, a second inclined surface 5111b, and a connecting surface 5111c.

The first inclined surface 5111a is an element which forms one surface of the ring portion 511 by being connected to the extending inclined surface 5113 and is slanted to the left toward a lower side. The second inclined surface 5111b is an element which forms the other surface of the ring portion 511 and is formed parallel with the first inclined surface 5111a at a certain distance. The connecting surface 5111c connects the first inclined surface 5111a to the second inclined surface 5111b and is preferably formed as a curved shape.

The extending inclined surface 5113 has a slope in the same direction with the first inclined surface 5111a and extends from the first inclined surface 5111a to form one side of the ring portion 511.

Because the bent protrusion 333 pushes the first inclined surface 5111a and the extending inclined surface 5113 one after another if the elevating portion 30 ascends, the moving member 51 rotates counterclockwise (the rotation direction of the opening and closing portion 50 is determined as clockwise or counterclockwise based on a view of the electronic cigarette viewed from the front side). The moving member 51 comes to a stop when the first inclined surface 5111a and the extending inclined surface 5113 does not move back by being disposed in parallel with the direction of ascent and descent of the elevating portion 30.

The connecting protrusion 513 protrudes from the rear side of the moving member 51 toward the rear-side casing 23 in an upper end of the moving member 51. The connecting protrusion 513 connected to the connecting member 53 rotates the connecting member 53 in connection with the rotation of the moving member 51.

The rotation guide protrusion 515 protrudes from the rear side of the moving member 51 toward the rear-side casing 23, guides the rotation of the moving member 51 by being inserted in the rotation guide protrusion groove of the rear-side casing 23 and may limit radius of rotation of the moving member 51 by adjusting length of the rotation guide protrusion groove 233.

The connecting member 53 is an element which transfers rotational force caused by the rotation of the moving member 51 to the door 55 and includes a lower portion 531, an upper portion, 533, a middle portion 537, and the rotation axis protrusion 535.

The lower portion 531 being an element connected to the moving member 51 straightly stretches from an end of the middle portion 537 down and includes a first connecting protrusion receiving groove 5311.

The first connecting protrusion receiving groove 5311 penetrates in a lower side of the lower portion 531 and is connected to the connecting protrusion 515 of the moving member 51, so the connecting member 53 rotates in an opposite direction to the rotation direction of the moving member 51 when the moving member 51 rotates.

The upper portion 533 being an element connected to the door 55 straightly stretches from the other side of the middle portion 537 up and includes a second connecting protrusion receiving groove 5331.

Because the second connecting protrusion receiving groove 5331 formed to penetrate in an upper side of the upper portion 533 is connected to the door 55, the door 55 moves in accordance with the rotation of the connecting member 53 and the opening 25 is opened or closed.

The middle portion 537 being an element connecting the upper portion 533 and the lower portion 531 is slanted to the right toward a down side. The middle portion 537 being slanted is to obtain a space d for opening the door 55 as shown in FIG. 15b.

The reason why the upper portion 533 and the lower portion 531 straightly stretch toward the up side and the down side, respectively, is that the space d can be obtained and spaces that the opening and closing portion 50 takes up inside the casing portion 20 can be reduced compared to a case where the upper portion 533 and the lower portion 531 extend with the same slope as the middle portion 537.

The rotation axis protrusion 535 protrudes to the front side and the rear side at a center of rotation of the connecting member 53. The rotation axis protrusion 535 in the front side is coupled to the guide protrusion fixing piece 45 and the rotation axis protrusion 535 in the rear side is coupled to the rotation axis protrusion groove 235 of the rear-side casing 23 such that the connecting member 53 rotates about the rotation axis protrusion 535 as an axis.

The door 55 is an element which opens or closes the opening 25 by rotation of the connecting member 53 and includes a cover plate 551, an extension plate 553, and a connecting protrusion 555.

The cover plate 551 is an element which covers the opening 25 as the elevating portion 30 descends and opens the opening 25 as the elevating portion 30 ascends and has a complementary shape to the cross section of the casing portion 20. It is preferable to form the cover plate 551 to be a certain size smaller than the cross section of the casing portion 20 since the cover plate 551 needs to open or close the opening 25 while moving inside the casing portion 20.

The extension plate 553 is a plate extending from a lower side of the cover plate 551 to the connecting member 53 and makes the connecting protrusion 555 protrude from the extension plate 553.

The connecting protrusion 555 protrudes at one side of the extension plate 553 and is coupled to the second connecting protrusion receiving groove 5331 of the connecting member 53. The connecting protrusion 555 opens the opening 25 by moving the cover plate 551 when the connecting member 53 rotates clockwise, while closing the opening 25 by moving the cover plate 551 when the connecting member 53 rotates counterclockwise.

With reference to FIGS. 15 to 17, a process of opening and closing the opening 25 by the opening and closing portion 50 in connection with the elevating portion 30 will be described in detail. In FIGS. 15 to 17, the front-side casing 21 is omitted for convenience; a is a back elevation of the electronic cigarette viewed from the rear side; and b is a front elevation of the electronic cigarette viewed from the front side.

If the user lifts the control protrusion 325 upward, the elevating portion 30 moves upward, which causes the moving member 51 to rotate counterclockwise by the bent protrusion 33 pushing the first inclined surface 5111a and the extending inclined surface 5113 of the moving member 51. During this time, the rotational motion of the moving member 51 is guided by the rotation guide protrusion 515 received in the rotation guide protrusion groove 233 of the rear-side casing 23.

As the moving member 51 rotates counterclockwise, the connecting member 53 connected to the moving member 51 by the connecting protrusion 515 rotates clockwise and the rotational motion of the connecting member 53 is guided by the rotation axis protrusion 535 received in the rotation axis protrusion groove 235 of the lower-side casing 23.

As the connecting member 53 rotates clockwise, the door 55 connected to the connecting member 53 by the connecting protrusion 555 moves in a direction of opening the opening 25. If the control protrusion 325 is moved farther upward, the opening 25 is in an opened state and the cartridge 63 of the smoke generating unit 60 protrudes to the outside of the casing portion 20.

If the user lowers the control protrusion 325 downward, the elevating body 321 moves downward. Then the cartridge 63 enters the inside of the casing portion 20, the bent protrusion 333 pushes the connecting surface 5111c of the moving member 51, and the moving member 51 rotates clockwise.

As the moving member 51 rotates clockwise, the connecting member 53 connected to the moving member 51 by the connecting protrusion 513 rotates counterclockwise. Linked to the connecting member 53, the door 55 moves in a direction of closing the opening 25 and closes the opening 25 when the cartridge 63 connected to the elevating body 321 enters the inside the casing portion 20.

As shown in FIGS. 4 and 18, the smoke generating portion 60 ascends or descends inside the casing portion 20, so the upper end protrudes to the outside of the casing portion 20 through the opening 25, generates smoke by vaporizing a stored solution, and includes a vaporizing portion 61 and the cartridge 63.

The vaporizing portion 61 is capable of generating smoke by vaporizing the solution stored inside the cartridge 53 through power supplied by the power supply portion 70 and includes a male screw thread 611 and an electrode 613.

The male screw thread 611 is disposed in a lower part of the vaporizing portion 61. The male screw thread 611 may be screw-fastened with a female screw thread 81 being inside the connector portion 80 described below in coupling the vaporizing portion 61 to the connector portion 80, which provides relatively strong coupling force compared to the coupling of the connector portion 80 to the support 31 due to characteristics of screw connection.

The electrode 513 being a part protruding downward from a center part of the male screw thread 611 is made of a conductive material and capable of supplying power to the vaporizing portion 61 from the power supply portion 80 by making contact with an upper side of the center pin 78 of the power supply portion 80 described below.

The cartridge 63 is capable of storing a solution inside, and the vaporizing portion 61 is coupled inside. The cartridge 63 vaporizes the stored solution through the vaporizing portion 61 and generates smoke and discharges the generated smoke through a suction portion (not shown) in a lower end of the cartridge 63 to the outside. The cartridge 63 preferably has a cylindrical shape extending vertically, but any shape is possible if the shape performs abovementioned functions.

As shown in FIG. 4 and FIGS. 19 to 22, the power supply portion 70 is disposed inside the casing portion 20 and supplies power to the smoke generating portion 60 and includes a battery 71, a battery connecting terminal 72, a switch 73, a charging terminal 74, a power supply terminal 75, a contact pin 76, a connecting terminal 77, a center pin 78 and a main circuit board 79.

To clearly describe power connection arrangement of the present invention, the battery 71, the battery connecting terminal 72, the power supply terminal 75, the contact pin 76, the connecting terminal 77, the center pin 78, and the electrode 613 are shaded dark in FIGS. 19 to 21, and flow of power are represented by arrows in FIGS. 20a and 21b for easy understanding.

The battery 71 supplies power for operating the electronic cigarette. Various types of batteries may be used but a secondary battery which is rechargeable and has a circular shape may preferably be used.

The battery connecting terminal 72 is formed to protrude in an upper side of the main circuit board 79 and connects the battery 71 to the main circuit board 79.

The switch 73 is formed in the main circuit board 79. When the user pushes the switch 73 while the power supply terminal and the contact pin 76 are in contact, power of the battery 71 is supplied to the smoke generating portion 60 under control of the main circuit board 79 and smoke is generated.

The charging terminal 74 is formed in a lower side of the main circuit board 79. One end of the charging terminal 74 is inserted in the charging terminal groove 215 and connected to an external power supply device (not shown) to receive power for charging the battery 71.

The power supply terminal 75 includes a first supply terminal 751 and a second supply terminal 752 and supplies power to the smoke generating portion 60 by being coupled to the contact pin 76 of the elevating portion 30. Although it is preferable to place the power supply terminal 75 in a location where the contact pin 76 is when the user lifts the elevating body portion 32, any position is possible if the abovementioned function can be performed.

The contact pin 76 includes a first contact pin 761 and a second contact pin 762. The contact pin 76 being a conductor corresponds to a part capable of connecting different elements through upper and lower ends. According to the present invention, the contact pin 76 connects power between the power supply terminal 75 and the connecting terminal 77.

The first contact pin 761 and the second contact pin 762 includes bodies 761a, 762a, pressurizing protrusions 761b, 762b, and elastic bodies 761c, 762c.

The bodies 761a, 762a have an inner space where the elastic bodies can be disposed and are provided in the contact pin coupling portion 323 of the elevating portion 30 to move up and down integrally with the elevating portion 30. One ends of the pressurizing protrusions 761b, 762b are inserted in the bodies 761a, 762a, and the other ends protrude upward. Accordingly, the pressurizing protrusions 761b, 762b electrically contact with the first supply terminal 751 and the second supply terminal 752 of the power supply terminal 75, respectively, as the elevating portion 30 ascends or are electrically disconnected as the elevating portion 30 descends. Lower ends of the bodies can be coupled to maintain electric communication with the first connecting terminal 771 of the connecting terminal 77 described below.

The elastic bodies 761c, 762c are disposed inside the bodies 761a, 762a and apply pressure to the pressurizing protrusions 761b, 762b upward. When the contact pin 76 does not make contact with the power supply terminal, an elongated state is maintained by the pressurizing protrusions 761b, 762b pressurized upward as 76a of FIG. 22a. When the contact pin 76 makes contact with the power supply terminal 75, a shrunk state is maintained by the pressurizing protrusions 761b, 762b pressurized downward as 76b of FIG. 22b. When the power supply terminal 75 and the contact pin 76 make contact in accordance with ascent of the elevating portion 30 and the contact is maintained by the opening and closing portion 50, the pressurizing protrusions 761b, 762b of the contact pin 76 are elastically pressurized upward by the elastic bodies 761c, 762c, thereby maintaining continuous contact with the power supply terminal 75. Accordingly, power is stably supplied by preventing release of the contact state under any circumstance.

The connecting terminal 77 being a conductor electrically connects between the contact pin 76 and the center pin 78. The connecting terminal 77 includes a first connecting terminal 771 and a second connecting terminal 772 and may have a plurality of connecting terminals based on internal structure of the electronic cigarette or types of the battery 71.

The first connecting terminal 771 includes a first contact pin receiving hole 771a, one end of which is coupled with an upper part of the first contact pin 761 to be electrically connected to the body 761a of the first contact pin and the other end of which is mounted on a step 316 of the support 31 to be grounded as described below.

The second connecting terminal 772 includes a center pin receiving hole 772b and a second contact pin receiving hole 772a. The center pin receiving hole 772b is electrically connected to the lower end part of the center pin 78, and the second contact pin receiving hole 772a is electrically connected to the body 762a of the second contact pin. Accordingly, the center pin 76 is electrically connected to the second contact pin 762 through the second connecting terminal and receives power.

The center pin 78 being a conductor is capable of connecting different elements through upper and lower ends, like the contact pin 76. The center pin 78 according to the present invention may connect power between the vaporizing portion 61 and the support 31 and includes a body 781, a pressurizing protrusion 782, and an elastic body 783.

The body 781 of the center pin 78 has a space inside which the elastic body 783 is disposed and is capable of moving up and down integrally with the elevating portion 30 by coupling to the center pin coupling portion 311. The pressurizing protrusion 782 connects or disconnects power by contacting with the electrode 611 of the vaporizing portion 61 described below. The body 781, the lower end of which is coupled to the center pin receiving hole 772b of the second connecting terminal 772, may make electric connection between the vaporizing portion 61 and the support 31 when the elevating portion 30 ascends and may release the electric connection when the elevating portion 30 descends.

In addition, the elastic body 783 stored in the body 781 elastically pressurize the pressurizing protrusions 782 upward. When the center pin 78 does not make contact with the vaporizing portion 61, an elongated state is maintained by the pressurizing protrusion 782 pressurized upward as 78a of FIG. 22a. When the center pin 78 makes contact with the vaporizing portion 61, a shrunk state is maintained by the pressurizing protrusion 782 pressurized downward as 78b of FIG. 22b. When the cartridge is coupled to the connector, the vaporizing portion 61 and the center pin 78 makes contact and the pressurizing protrusion 782 of the center pin 78 is elastically pressurized upward by the elastic body 783, thereby maintaining continuous contact with the vaporizing portion 61. Accordingly, power is stably provided by preventing release of the contact state under any circumstance.

As shown in FIG. 18, the power supply portion 70 according to the present invention transfers power supplied from the battery 71 through the power supply terminal 75, the contact pin 76, the connecting terminal 77, and the center pin 78 to the vaporizing portion 61 inside the smoke generating portion 60. Such connection arrangement and transfer process of power can be easily recognized by referring to shaded areas and arrows in FIGS. 19 to 21.

That is, the present invention provides a structure where power is connected through the coupling relationship between each element without using wires. Internal structures are made simple and robustness and durability in power connection is improved in comparison to a case where power is connected using wires.

In addition to managing power connection by controlling the switch 73, according to the present invention, power can be connected only when the elevating portion 30 ascends and power can be physically shut off when the elevating portion 30 is lowered by connecting or disconnecting electrical contact between the power supply terminal 75 and the connector pin 76 through vertical movement of the elevating portion 30. Therefore, utilization efficiency of the battery 71 and the electronic cigarette can be improved by preventing the battery from being discharged, which may occur by electrical connection maintained even when the power of the electronic cigarette is turned off.

The main circuit board 79 is configured to control voltage supplied to the smoke generating portion 60 such that the user can control the vaporization amount based on preference of the user. Below, elements of the main circuit board 79 and an operating process thereof are described in detail.

As shown in FIG. 24, the main circuit board 79 controlling electrical operation of the electronic cigarette controls power supply to the smoke generating portion 60 and charging of the battery 71. The main circuit board 79 includes a control portion 791, a voltage converting portion 793 and an operation indicating portion 795.

The control portion 791 controls the voltage converting portion 793 to convert a constant voltage supplied from the battery 71 into a voltage capable of supplying the vaporization amount set by the user. Below described is a process of setting the vaporization amount that the user wants through the control portion 791.

As shown in FIG. 25, the electronic cigarette according to the present invention comprises: a power turned on step S1 which turns on power of the electronic cigarette, a power supply step S2 allowing smoking using the electronic cigarette, a voltage control step S3 which allows the vaporization amount of the electronic cigarette to be controlled, a power turned off step S4 which can turn off power, and a power shut off step S5 which can prevent discharge by completely shutting off power.

In the power turned on step S1, power of the electronic cigarette can be turned on S14 by lifting the elevating portion S12 in a power turned off state S11 in which power is completely turned off and then touching the switch five times S13. If the elevating portion is not lifted, power is in a cut off state as the power supply terminal 75 and the contact pin 76 do not make contact. Accordingly, the power is not turned on even though the switch is touched five times.

The power supply step S2 supplies power S22 to the power supply portion 70 when the switch 73 is being pushed continuously S21 after completion of the power turned on step S1.

Through the voltage control step S3, the level of voltage supplied to the smoke generating portion 60 is controlled S32 when the switch is additionally pushed three times S31 after completion of the power turned on step S1 and the vaporization amount changes based on the level of the supplied voltage, so the user can choose and use the vaporization amount suitable for oneself. However, since the abovementioned method for controlling the vaporization amount of the electronic cigarette is merely an example, it should be clearly understood that the scope of the present invention is not limited thereto.

Through the power turned off step S4, power of the electronic cigarette is turned off when the switch 73 is again touched five times S42 after completion of the power supply step S1 which is completed by lifting the elevating portion 30 and touching the switch 73 five times and the power supply step S2 maintained by continuously pushing the switch 73. Even after the power turned off step S4 is finished, the battery 71 may be discharged even in the power turned off state as the power supply terminal 75 and the contact pin 76 are in contact as far as the elevating portion 30 is in a lifted state.

The power shut off step S5, as a step where power of the electronic cigarette is shut off S52 by lowering S51 the elevating portion 30 after completion of the power turned off step S4, physically separates the power supply terminal 75 and the contact pin 76 through descent of the elevating portion 30. Accordingly, discharge of the battery 71 is prevented by thoroughly preventing power connection in case the electronic cigarette is not used and utilization efficiency of the battery 71, as well as the electronic cigarette according to the present invention, can be enhanced.

As shown in FIG. 24, the voltage converting portion 793 receives information on the voltage set by the user from the control portion 791 and converts the certain voltage supplied by the battery 71 into the voltage received from the control portion 791. For example, assume that the battery 71 supplies a specific voltage of 3.7V and the levels set by the control portion 71 is: a Hi level of the vaporization amount being 4.3V, a Me level of the vaporization amount being 4.0V, and a Lo level of the vaporization amount being 3.7V. In such case, if the user sets a Hi level of the vaporization amount by using the abovementioned control method, the voltage converting portion 793 receives the information from the control portion 791, converts the supplied voltage of 3.7V to 4.3V, and supplies 4.3V to the smoke generating portion 60, thereby generating the amount of vaporization set by the user. The voltage converting portion 793 may preferably be a DC-to-DC converter but may be any element if the abovementioned function can be performed. Since setting the vaporization amount as said specific Hi, Me, and Lo values in the above is an example, it should be understood that the scope of the present invention is not limited thereto.

The operation indicating portion 795 is an element which enables the user to visually recognize information on the vaporization amount set by oneself. For instance, the operation indicating portion 795 may be an LED device which represents the Hi level of vaporization amount as red, the Me level of vaporization amount as blue, and the Lo level of vaporization amount as white.

As shown in FIG. 23, the connector portion 80 is a part which connects between the smoke generating portion 60 and the elevating portion 30 by the upper end connected to the smoke generating portion 60 and the lower end connected to the elevating portion 30. The connector portion 80 includes a female screw thread 81, an outer screw thread 82, the support insertion portion 83, the support insertion groove 84, and the support coupling portion 85.

The female screw thread 81 is formed in an inner face of the upper connector portion 80 and can be screw-fastened with the male screw thread 611 in the lower part of the vaporization portion 61. The female screw thread 81 can, thus, fix the connection between the vaporization portion 61 and the connector portion 80 and provide relatively strong coupling force due to the screw connection, compared to the coupling between the connector portion 80 and the support 31.

The outer screw thread 82 is a part which is formed in an outer face of the upper part of the connector portion 80. The female screw thread 613 may be formed in the vaporization portion 61 for the smoke generating portion 60, while the screw thread may be formed in the inner face of the lower part of smoke generating portion 60. Accordingly, even for the case where the smoke generating portion 60 has the latter shape, the outer screw thread 82 may additionally be formed to facilitate the connection between the smoke generating portion 60 and the connector portion 80.

The support insertion portion 83 protrudes in a horizontal direction in an upper side of the support coupling portion 85. The support insertion portion 83 allows the connector fixing portion 315 to be received inside the support insertion groove 84 in the horizontal direction and coupled to each other in coupling the support 31 and the connector portion 80. After the coupling, the connector portion 80 is rotated such that the connector fixing portion 315 fixes the support insertion portion 83 by pushing, thereby fixing the connection between the connector portion 80 and the support 31.

A part of the support insertion groove 84 is depressed inward by a certain depth inside the support insertion portion 83. Coupling the connector portion 80 and the support 31 is achieved by the protrusions 3151 protruding inward in a plan view being engaged with the support insertion groove 84 in the horizontal direction and being inserted in the vertical direction.

The support coupling portion 85 is a protrusion protruding downward of the connector portion 80. The support coupling portion 85 is inserted in the connector insertion groove 314 in the vertical direction for coupling. After such coupling, the connector portion 80 can be rotated inside the inner space of the connector insertion groove 314. The support insertion portion 83 is firmly fixed in the support 31 by the rotation of connector portion 80 and subsequent pressing by the other end 3151a-2 of the inclined surface of the connector fixing portion 315.

With reference to FIG. 9, the coupling relationship between the elevating portion 30 and the connector portion 80 is described in detail.

As shown in FIG. 9a, the elevating portion 30 and the connector portion 80 are connected in a way that the lower end of the connector portion 80 is inserted in the upper end of the support 31 of the elevating portion 30. More specifically, the connector portion 80 is rotated in the horizontal direction such that the connector fixing portion 315 and the support insertion groove 84 are engaged with each other on a plane and vertical insertion of the connector portion 80 is accomplished.

As shown in FIG. 9b, the support coupling portion 85 is inserted in the connector insertion groove 314 while the connector portion 80 is being rotated.

As shown in FIGS. 9c and 10a, the support coupling portion 85 is completely inserted in the connector insertion groove 314 and mounted.

Then, as shown in FIGS. 9d and 10b, if the connector fixing portion 315 stays engaged with the support insertion groove 84 in the horizontal direction, the connector portion 80 may move in the vertical direction. To prevent this, the connection between the support 31 and the connector portion 80 is fixed in the vertical direction by again rotating the connector portion 80 in the horizontal direction.

In the above, the applicant described preferred embodiments of the present invention. It should be interpreted that such embodiments are merely examples which implement the technical idea and any modification or revision falls within the scope of the prevent invention if it implements the technical idea of the present invention, however.

The invention claimed is:

1. An electronic cigarette, comprising:
    a smoke generating portion which generates smoke of the electronic cigarette;
    an elevating portion coupled to the smoke generating portion to be movable in a vertical direction; and
    a power supply portion which supplies power to the smoke generating portion through the elevating portion, the power supply portion including a battery which generates electrical energy to supply power, a main circuit board electrically connected to the battery, a power supply terminal electrically connected to the main circuit board, and a connecting pin being a conductor and ascending or descending by being provided in the elevating portion in a state of being electrically connected to the smoke generating portion,
    wherein the connecting pin is connected to the power supply terminal and in electrical communication when the elevating portion ascends, the connecting pin is electrically disconnected by being separated from the power supply terminal when the elevating portion descends, and after the descent power supply to the smoke generating portion is shut off.

2. The electronic cigarette of claim 1, wherein the power supply portion further comprises a center pin mounted on the elevating portion,
    wherein the main circuit board controls electrical operation of the electronic cigarette, wherein the connecting terminal is provided in the elevating portion.

3. The electronic cigarette of claim 2, wherein the connecting terminal being a conductor comprises: a first connecting terminal and a second connecting terminal, and the connecting pin comprises: a first connecting pin and a second connecting pin,
    wherein the first connecting terminal contacts with the first connecting pin to be grounded, and the second connecting terminal contacts with the second connecting pin and the center pin to maintain electrical communication.

4. The electronic cigarette of claim 3, wherein the first connecting terminal includes a first connecting pin receiving hole and is coupled to the first connecting pin, and the second connecting terminal includes a center pin receiving hole and a second connecting pin receiving hole,
    wherein the center pin receiving hole is coupled to the center pin and the second connecting pin receiving hole is coupled to the second connecting pin such that the center pin and the second connecting pin are in electrical communication.

5. The electronic cigarette of claim 4,
    wherein one end of the first connecting pin is electrically connected to the first connecting pin receiving hole of the first connecting terminal and an end of the second connecting pin is electrically connected to the second connecting pin receiving hole such that the connecting pin electrically contacts with the power supply terminal when the elevating portion ascends and electrical contact is released when the elevating portion descends.

6. The electronic cigarette of claim 1,
    wherein the connecting pin and the center pin includes an elastic body inside such that: the connecting pin and the center pin are capable of being elastically compressed or elastically restored in a vertical direction; electrical communication is well maintained by pressurizing the power supply terminal by the elastic body of the connecting pin when the connecting pin contacts with the power supply terminal as the elevating portion ascends; and electrical communication is well maintained by pressurizing the smoke generating portion by the elastic body of the center pin when the center pin contacts with the smoke generating portion,
thereby enabling stable power connection state of the electronic cigarette.

7. The electronic cigarette of claim 6, wherein the elevating portion comprises: a support which supports a lower part of the smoke generating portion; and an elevating body portion formed at one side of the support to control vertical motion of the elevating portion,
  wherein the elevating body portion includes a connecting pin coupling portion capable of receiving the connecting pin inside for coupling, and the connecting pin is inserted in the connecting pin coupling portion and coupled to the elevating portion to be in vertical motion integrally with the elevating portion.

8. The electronic cigarette of claim 7, wherein the support includes a center pin coupling portion capable of receiving the center pin for coupling and formed at an upper end,
  wherein the center pin is inserted in the center pin coupling portion to be coupled to the support and is capable of moving integrally with the support in the coupling state.

9. The electronic cigarette of claim 1, further comprising a connector portion which connects between the smoke generating portion and the elevating portion,
  wherein an upper end of the connector portion is connectable to the smoke generating portion and a lower end of the connector portion is connectable to a support.

10. The electronic cigarette of claim 9, wherein the connector portion comprises a support coupling portion, and
  the support comprises a connector coupling portion protruding upward from a center part of an upper end; and a connector insertion groove by which the support coupling portion is inserted in an outer side of the connector coupling portion, thereby coupling the connector portion with the support as the support coupling portion is inserted in the connector insertion groove while the connector coupling portion is received for coupling in an inner space that the support coupling portion forms.

11. The electronic cigarette of claim 10,
  wherein the connector portion comprises: a support insertion portion protruded in a horizontal direction in an upper side of the support coupling portion; and a support insertion groove, a part of which is depressed inward by a certain depth inside the support insertion portion,
  wherein the support includes a connector fixing portion protruded upward along the periphery of the upper part of the support, the connector fixing portion including a protrusion, a part of which is protruded toward the center part of the support on a plane,
  wherein the connector fixing portion is received for coupling in a horizontal direction into the support insertion groove in coupling the connector portion to the support, and after coupling the connector portion is rotated such that the connector fixing portion presses and fixes the support insertion portion, thereby fixing the coupling of the connector portion and the support.

12. The electronic cigarette of claim 11, wherein the protrusion of the connector fixing portion includes an inclined surface inclined along a circumferential direction at the lower end, one end of the inclined surface having height lower than the other end,
  wherein when the connector portion is inserted in the support and rotated, the support insertion portion proceeds to the other end through the one end of the inclined surface and is pressed by the other end of the inclined surface, whereby the connector is firmly fixed to the support.

13. The electronic cigarette of claim 1, further comprising a switch configured to supply power to the smoke generating portion when being pushed under control of the main circuit board in a state where the connecting pin is in contact with the power supply terminal.

* * * * *